US012697432B2

(12) United States Patent
Burren et al.

(10) Patent No.: US 12,697,432 B2
(45) Date of Patent: Aug. 4, 2026

(54) ASSEMBLY FOR A CARTRIDGE NEEDLE INSERTION MECHANISM

(71) Applicant: Ypsomed AG, Burgdorf (CH)

(72) Inventors: Stefan Burren, Schwarzenburg (CH);
Mario Bernhard, Burgdorf (CH);
Andres Mellenberger, Koppigen (CH);
Markus Tschirren, Burgdorf (CH);
Susanne Schenker, Aarwangen (CH);
Christian Schrul, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 1143 days.

(21) Appl. No.: 17/724,162

(22) Filed: Apr. 19, 2022

(65) Prior Publication Data

US 2022/0241497 A1 Aug. 4, 2022

Related U.S. Application Data

(63) Continuation of application No. PCT/EP2020/079537, filed on Oct. 21, 2020.

(30) Foreign Application Priority Data

Oct. 31, 2019 (EP) ..................................... 19206382

(51) Int. Cl.
*A61M 5/142* (2006.01)
*A61M 5/162* (2006.01)
*A61M 5/28* (2006.01)

(52) U.S. Cl.
CPC ........ *A61M 5/14248* (2013.01); *A61M 5/162* (2013.01); *A61M 5/285* (2013.01); *A61M 2005/14252* (2013.01)

(58) Field of Classification Search
CPC .. A61M 5/14248; A61M 5/162; A61M 5/285; A61M 2005/14252; A61M 39/14;
(Continued)

(56) References Cited

U.S. PATENT DOCUMENTS 6,474,219 B2 11/2002 Klitmose et al.
9,107,999 B2 8/2015 Moberg et al.
(Continued)

FOREIGN PATENT DOCUMENTS

DE 102004059491 A1 7/2006
EP 3260149 * 12/2017
(Continued)

OTHER PUBLICATIONS

Extended European Search Report issued in European Application No. 19206382.4, mailed on Mar. 24, 2020, 9 pages.
(Continued)

*Primary Examiner* — Theodore J Stigell
(74) *Attorney, Agent, or Firm* — Dorsey & Whitney LLP

(57) ABSTRACT

An assembly for a cartridge needle insertion mechanism includes a housing, a cartridge needle defining a cartridge needle axis and a cartridge closed by a septum. A cartridge needle slider is linearly guided by the housing along an insertion axis to be moved by a driver from a first position, where the cartridge needle is not penetrating the septum, to a second position where the cartridge needle penetrates the septum of the cartridge. A cartridge needle holder holding the cartridge needle is operatively coupled with the cartridge needle slider to be moved with the cartridge needle slider from the first to the second position. The assembly includes a compliant coupling between the cartridge needle holder and the cartridge needle slider configured to facilitate movement of the cartridge needle holder with respect to the slider when moved into the second position, thereby compensating for needle penetration forces.

15 Claims, 17 Drawing Sheets

(58) Field of Classification Search

CPC .... A61M 2005/2407; A61M 2005/312; A61M 2005/3121; A61M 5/2455; A61M 5/3134; A61M 5/3204; A61M 5/1456

See application file for complete search history.

(56) References Cited

U.S. PATENT DOCUMENTS

| | | |
|---|---|---|
| 2008/0051738 A1 | 2/2008 | Griffin |
| 2009/0093792 A1 | 4/2009 | Gross et al. |
| 2009/0099521 A1 | 4/2009 | Gravesen et al. |
| 2010/0063443 A1 | 3/2010 | Lin |
| 2011/0166512 A1 | 7/2011 | Both et al. |
| 2011/0306929 A1 | 12/2011 | Levesque et al. |
| 2012/0035546 A1 | 2/2012 | Cabiri |
| 2012/0123344 A1 | 5/2012 | Hornig et al. |
| 2013/0006213 A1 | 1/2013 | Arnitz et al. |
| 2013/0060233 A1 | 3/2013 | Oconnor et al. |
| 2013/0253431 A1 | 9/2013 | Kaufmann et al. |
| 2014/0163526 A1 | 6/2014 | Cabiri et al. |
| 2016/0256352 A1 | 9/2016 | Bar-el et al. |
| 2016/0256353 A1* | 9/2016 | Bar-El .............. A61M 5/14248 |
| 2017/0100305 A1 | 4/2017 | Moia et al. |
| 2017/0354783 A1 | 12/2017 | Gazeley et al. |
| 2018/0008769 A1 | 1/2018 | O'connor et al. |
| 2018/0028747 A1 | 2/2018 | Hanson et al. |
| 2018/0236173 A1 | 8/2018 | Mccaffrey et al. |
| 2019/0117880 A1 | 4/2019 | Hirschel et al. |
| 2019/0160225 A1 | 5/2019 | Verlaak et al. |
| 2020/0023122 A1 | 1/2020 | Mccullough et al. |
| 2020/0155759 A1 | 5/2020 | Hanson et al. |
| 2021/0138151 A1 | 5/2021 | Scheurer et al. |

FOREIGN PATENT DOCUMENTS

| | | |
|---|---|---|
| EP | 3260149 A1 | 12/2017 |
| EP | 3348284 A2 | 7/2018 |
| EP | 3067083 B1 | 12/2018 |
| EP | 3539592 A1 | 9/2019 |
| EP | 3603700 A1 | 2/2020 |
| EP | 3656419 A1 | 5/2020 |
| GB | 2552340 A | 1/2018 |
| WO | 9509021 A1 | 4/1995 |
| WO | 0183008 A1 | 11/2001 |
| WO | 0240083 A2 | 5/2002 |
| WO | 2004056411 A2 | 7/2004 |
| WO | 2005002649 A1 | 1/2005 |
| WO | 2006108809 A1 | 10/2006 |
| WO | 2007038059 A2 | 4/2007 |
| WO | 2010029054 A1 | 3/2010 |
| WO | 2011012465 A1 | 2/2011 |
| WO | 2011046850 A1 | 4/2011 |
| WO | 2011046950 A1 | 4/2011 |
| WO | 2013140395 A1 | 9/2013 |
| WO | 2015032747 A1 | 3/2015 |
| WO | 2016053954 A1 | 4/2016 |
| WO | 2017089286 A1 | 6/2017 |
| WO | 2017219154 A1 | 12/2017 |
| WO | 2017219155 A1 | 12/2017 |
| WO | 2018024625 A1 | 2/2018 |
| WO | 2020026049 A1 | 2/2020 |
| WO | 2021083746 A1 | 5/2021 |

OTHER PUBLICATIONS

International Search Report and Written Opinion issued in International Patent Application No. PCT/EP2020/079537, issued on Jan. 18, 2021, 11 pages.

International Search Report and Written Opinion received for International Application No. PCT/IB2019/055544, mailed on Jul. 29, 2019, 9 pages.

International Preliminary Report on Patentability received for International Application No. PCT/IB2019/055544, mailed on Feb. 11, 2021, 7 page.

Extended European Search Report received for European Patent Application No. 18186224.4, mailed on Nov. 9, 2018, 6 pages.

Extended European Search Report, issued in EP16175887.5 on Dec. 23, 2016, 8 pages.

* cited by examiner

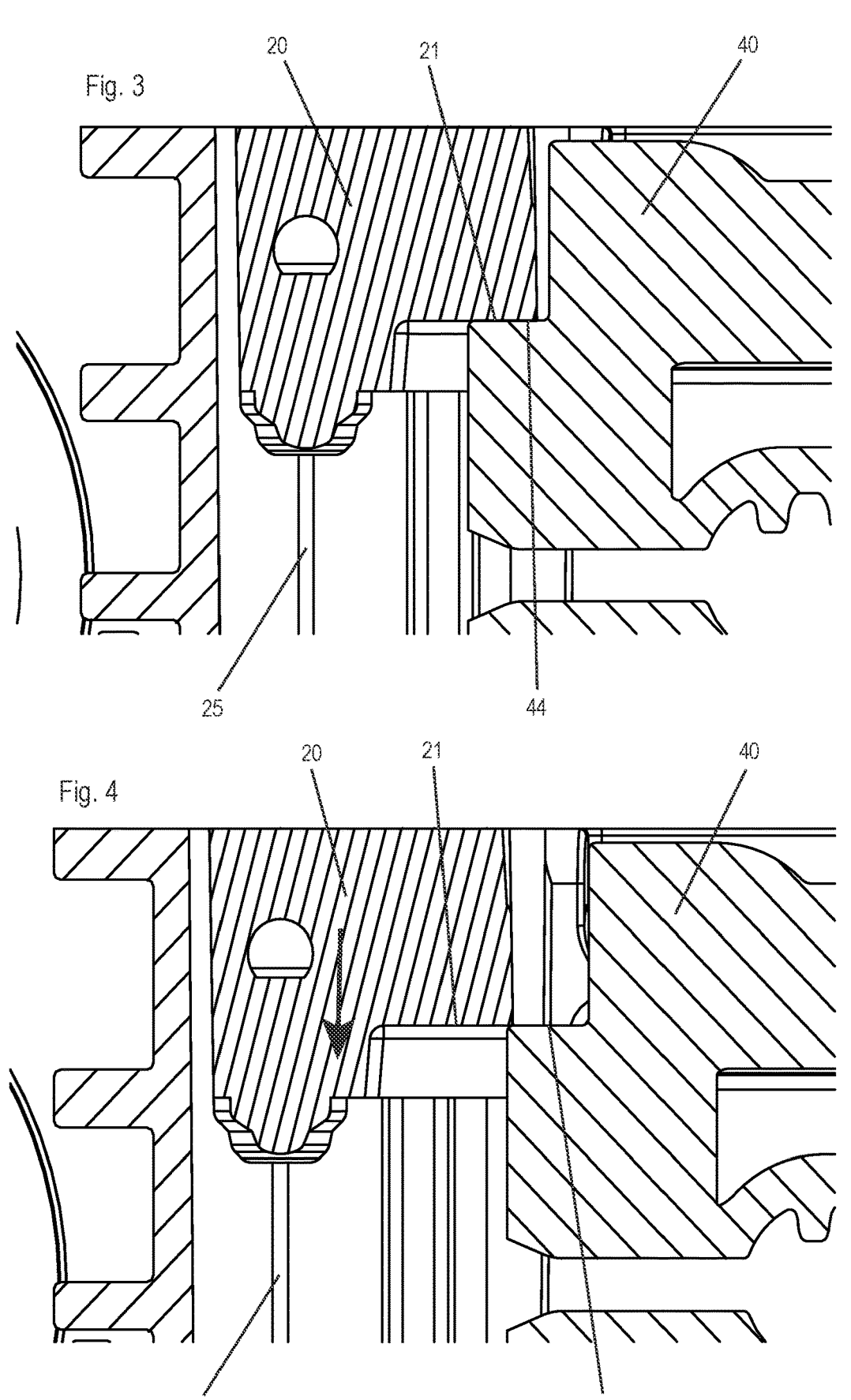

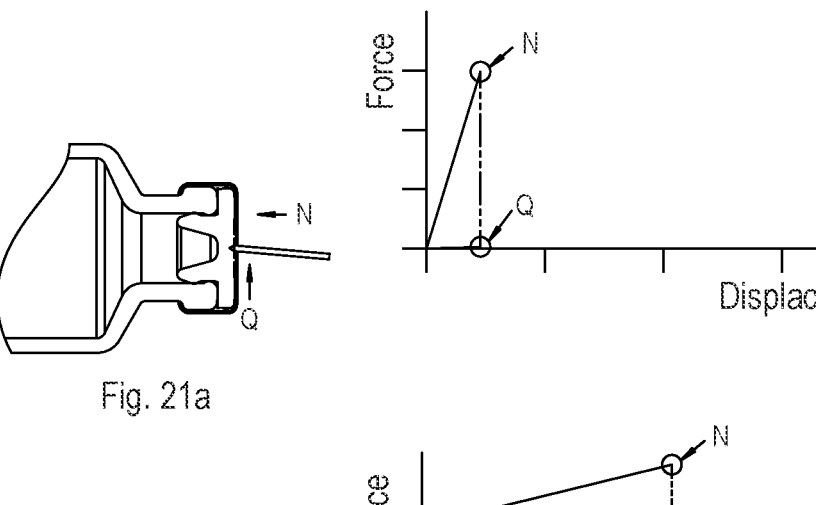
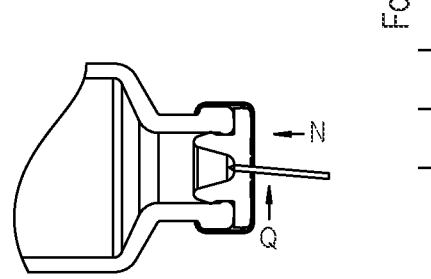
Fig. 21a
Fig. 21a'
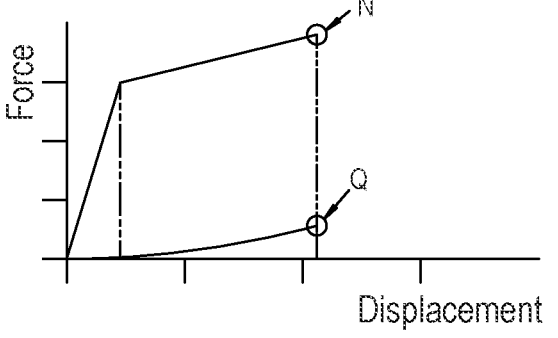
Fig. 21b
Fig. 21b'
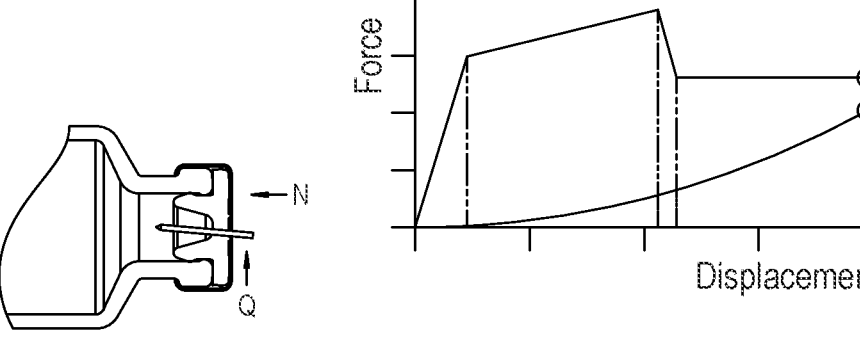
Fig. 21c
Fig. 21c'
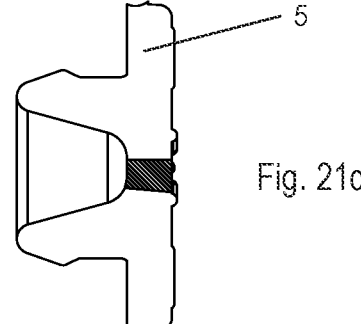
Fig. 21d

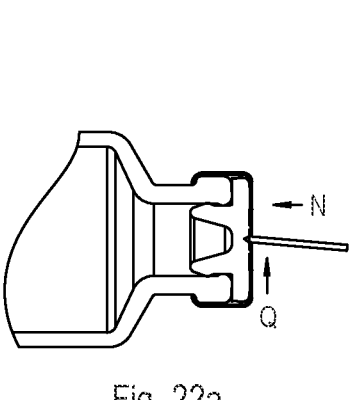
Fig. 22a
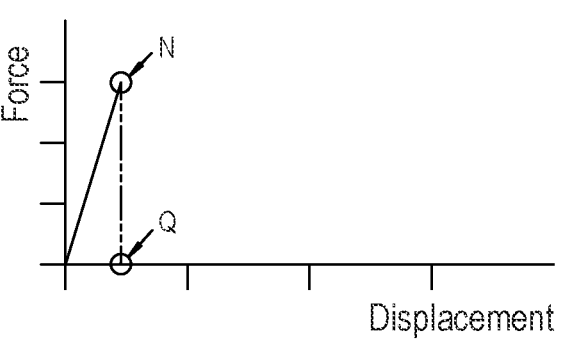
Fig. 22a'
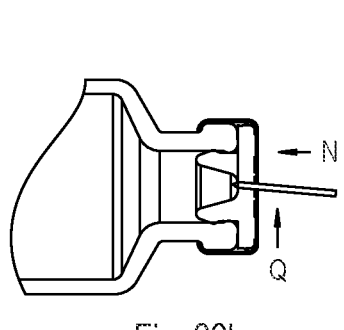
Fig. 22b
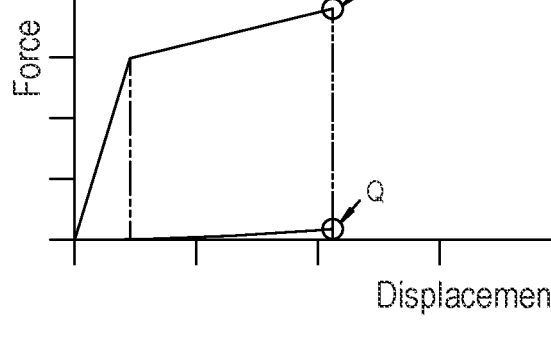
Fig. 22b'
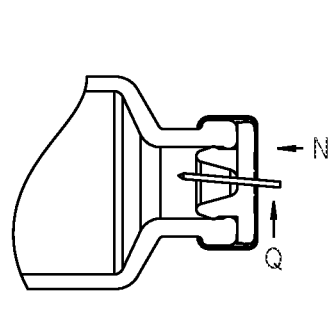
Fig. 22c
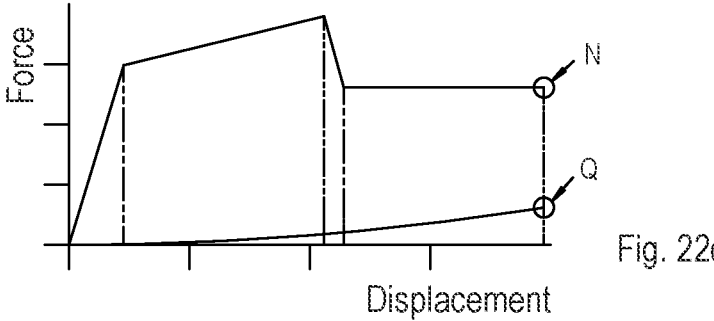
Fig. 22c'
Fig. 22d

ASSEMBLY FOR A CARTRIDGE NEEDLE INSERTION MECHANISM

CROSS REFERENCE TO RELATED APPLICATIONS

This application claims priority to International Patent Application No. PCT/EP2020/079537, filed Oct. 21, 2020, entitled "AN ASSEMBLY FOR A CARTRIDGE NEEDLE INSERTION MECHANISM," which in turn claims priority to European Application No. 19206382.4, filed Oct. 31, 2019, entitled "AN ASSEMBLY FOR A CARTRIDGE NEEDLE INSERTION MECHANISM", each of which is incorporated by reference herein, in their entirety and for all purposes.

TECHNICAL FIELD

Implementations relate to assemblies for a cartridge needle insertion mechanism including a cartridge needle slider configured to move a cartridge needle holder holding a needle such that a septum of a cartridge is penetrated by the needle.

BACKGROUND

Fluid medicaments are delivered from a reservoir containing the medicament to patients either via intravenous or subcutaneous injection. A piston or plunger in the reservoir is advanced by a delivery mechanism towards an outlet of the reservoir such that the medicament located between the piston and the outlet can be injected via a needle that is inserted into the patient. The reservoir selected is often a cartridge such as a glass cartridge which is commonly used in the pharmaceutical industry as a primary packaging material. The cartridge includes a glass barrel enclosing the medicament between the piston on one side and a septum on the opposite side. For delivery, a conduit for the fluid must be connected to the medicament in the cartridge on one end and a skin needle on the other end. The connection to the medicament in the cartridge may be established by piercing either the piston or the septum with a cartridge needle. The fluid connection to the cartridge may be established just before injection, e.g., the fluid conduit is not connected to the cartridge during storage of the product, or alternatively, a permanent fluid connection is present throughout the lifecycle of the product.

The fluid medicaments may be delivered to patients using an injection or infusion device including the delivery mechanism, the cartridge and the fluid conduit including the skin needle and the cartridge needle. Additionally, the injection or infusion device may have a needle insertion mechanism for automatic insertion of the skin needle into the skin of the patient. The other end of the fluid conduit with the cartridge needle may be connected to the cartridge just before use having the advantage that there is less risk of contamination of the medicament by components of the fluid conduit (leachables) as there is only contact for a limited time period during injection. Additionally, fill-finish of the product is separate from the assembly with the fluid conduit. The cartridge may thus be filled in a standardized sterile environment and the assembly of the device with the filled cartridge and the delivery mechanism including the fluid conduit may be performed under non-sterile clean room conditions making the assembly easier.

If the cartridge needle (connected to the conduit) is inserted into the cartridge just before using the injection or infusion device, then the cartridge may already be present in a so-called "ready-to-use" device or, alternatively, the user inserts the cartridge into an empty cartridge holder of the device and establishes the connection between the cartridge and the cartridge needle, for example, by closing the device. In some applications, relatively expensive medicaments are delivered by the device and a "ready-to-use" device is preferred by the pharmaceutical industry since it increases the reliability of the therapy and prevents loss of medicament due to handling failures during cartridge insertion into the holder or cartridge fracture.

In "ready-to-use" devices, the connection between the cartridge needle and the cartridge may be established by moving the cartridge in a cartridge holder versus a fixed cartridge needle thereby penetrating the septum (or piston) of the cartridge. The cartridge may be moved in the cartridge holder towards the needle using a cartridge insertion mechanism that automatically advances the cartridge (for example by a spring) or the user manually advances the cartridge in the holder. Alternatively, the cartridge needle is moved by a cartridge needle insertion mechanism that automatically inserts the cartridge needle in the septum of a cartridge that is axially fixed in the cartridge holder.

An example of a "ready-to-use" device is a bolus or patch injector as presented in EP 3067083 B1 where a cartridge is moved towards a collar including the cartridge needle to establish a fluid connection. In EP 3539592 A1, an example is shown for a "ready-to-use" device where a cartridge needle is moved towards a cartridge that is axially fixed in the cartridge holder.

A problem of devices where the fluid connection is established just prior to use (e.g., with no connection during storage) is that the needle may penetrate the septum under an angle that is not perpendicular to the septum. As the sharp needle tip cuts through the septum the penetration hole may be enlarged and off-axis needle penetration forces may act on the needle such that the liquid medicament may leak through the interface between the cartridge needle and the septum. This may waste expensive medicament and lead to under-dosing as part of the medicament cannot flow through the fluid conduit into the patient.

For devices where the cartridge is moved versus a fixed cartridge needle, e.g. either "ready-to use" or where the patient moves the cartridge in the cartridge holder, the off-axis insertion is exacerbated by the movement of the cartridge with respect to a cartridge holder. Especially for glass cartridges that have relatively low dimensional tolerances inherently linked to material and manufacturing methods. The movement of the cartridge versus a cartridge holder (often made from materials and methods having higher dimensional tolerances) results in misalignment of the cartridge with respect to the needle. In EP 3067083 B1, this problem is solved by a compliant support that aligns the collar including the cartridge needle with the cartridge. The cartridge is moved with respect to the collar and the collar is aligned with the cartridge as the collar engages the cartridge. Misalignment of the cartridge needle with respect to the collar cannot be compensated and this aspect still may lead to leakage. In EP 3539592 A1, the cartridge needle is moved by a cartridge needle slider towards the fixed cartridge. Any off-axis insertion of the cartridge needle is not compensated for, potentially leading to leakage and loss of medicament.

SUMMARY

It is an objective to provide an assembly for a cartridge needle insertion mechanism where a cartridge needle is moved towards, and inserted into, a fixed cartridge and to reduce the leakage risk due to off-axis septum penetration.

This objective is solved according to the present disclosure by providing a compliant coupling between a cartridge needle holder holding the cartridge needle and a cartridge needle slider. A driver may move the cartridge needle slider together with the holder and the needle towards the cartridge. The compliant coupling between slider and holder may facilitate movement of the cartridge needle holder (with the needle) with respect to the cartridge needle slider when moved into the second position thereby compensating for needle penetration forces that are directed perpendicular to the insertion direction.

According to the present disclosure, provided is an assembly for a cartridge needle insertion mechanism. The assembly may include a housing, which may be the main housing or a housing part connected to the main housing, a cartridge needle defining a cartridge needle axis and a cartridge closed by a septum. The cartridge may be a glass cartridge or be made from a plastic material such as a cycloolefinic copolymer (COC). Furthermore, the assembly may include a cartridge needle slider which may be linearly guided by the housing along an insertion axis such that the slider may be moved by a driver from a first position, where the cartridge needle is not penetrating the septum, to a second position where the cartridge needle penetrates the septum of the cartridge.

A cartridge needle holder may hold the cartridge needle and the cartridge needle holder may be operatively coupled with the cartridge needle slider to be moved together with the cartridge needle slider along the insertion axis from the first position to the second position. As the cartridge needle slider is moved by the driver towards the second position, the cartridge needle holder with the needle may also be slaved towards the second position. The assembly includes a compliant coupling that is structurally or functionally located between the cartridge needle holder and the cartridge needle slider. The compliant coupling may be resilient and capable of absorbing, reducing or counteracting forces directed to the coupling member or to coupling members forming the compliant coupling. The coupling member may be a coupler, a coupling means or a coupling part. Examples of a coupling member may be resilient arm, a pivoting arm or a pivoting surface, a hook, a tooth, hooks and teeth at the end of a flexible arm, a surface intended for frictional contact with a counter surface, a magnet (acting with a counter magnet), an electromechanical coupling member, an elastic member, a part of a dash-pot or a shock absorber or a viscous fluid. The compliant coupling may be configured to facilitate movement of the cartridge needle holder with respect to the cartridge needle slider when moved into the second position, thereby at least partially compensating, reducing or absorbing needle penetration forces. For instance, the compliant coupling may compensate, reduce or absorb needle penetration forces oriented perpendicular to the insertion axis.

The cartridge needle may move from the first position to the second position and the needle with its needle axis may enter the septum off-axis or oblique to the insertion axis. Reasons for the off-axis entrance may be due to the fast movement (e.g., moment of inertia) of the cartridge needle, or due to dimensional tolerances of the linear guide of the cartridge needle slider or because of an off-axis inserted/installed needle in the cartridge needle holder. This may have several effects: i) the tip of the needle cuts through the septum thereby enlarging the entrance hole for the needle, or ii) the needle may bend during penetration, giving rise to elastic forces acting on the needle which may be oriented perpendicular to the insertion axis, or iii) forces may act from the elastic septum onto the needle when the needle has penetrated the septum at an angle deviating from, e.g., not being parallel to, or coincident with, the insertion axis. These forces may be directed along the insertion axis, or may be partially directed perpendicular to the insertion axis. If not compensated for, or reduced, then the forces, or force components acting perpendicular to the insertion axis (effects ii and iii) and/or the enlarged entrance hole (i), may promote leakage of medicament from the cartridge to the ambient (e.g., to the exterior of the septum) along the interface between the needle and the septum. The insertion forces directed perpendicularly may transmit from the septum to the needle and subsequently to the needle holder such that the complaint coupling between the cartridge needle holder and the cartridge needle slider may be deformed thereby absorbing, reducing or compensating these forces and the cartridge needle holder may be displaced with respect to the cartridge needle slider. The cartridge needle slider may be linearly guided by the housing along the insertion axis, the guidance being perpendicular to the off-axis forces acting on the needle and therewith these forces are finally guided to the housing. The compliant coupling therewith may reduce or eliminate the risk of leakage and may improve the reliability of the device including the cartridge needle insertion mechanism.

The compliant coupling may be configured to facilitate movement of the cartridge needle holder with respect to the cartridge needle slider when the slider is moved into the second position. This movement of the cartridge needle holder with respect to the cartridge needle slider may be a lateral movement, or may be a movement perpendicular to the insertion axis, or the movement may be a pivoting movement of the cartridge needle holder around the insertion axis, or the cartridge needle holder may rotate around the insertion axis.

In the example mentioned previously, at least two sources, ii) and iii) are mentioned resulting in a force acting on the needle when inserted at an angle deviating from the insertion axis and which result in a force, or a force component acting on the needle and oriented perpendicular to the insertion axis. Alternatively and additionally, also torque can be exerted onto the needle which may be compensated for by a pivoting or rotational movement of the cartridge needle holder versus the cartridge needle slider and the compliant coupling may compensate those forces as well.

The compliant coupling may include a first coupling member (or first coupler or first coupling part or first coupling means) on the cartridge needle holder engaging a second coupling member (or second coupler or second coupling part or second coupling means) on the cartridge needle slider arranged in a plane parallel to the insertion axis.

The first coupling member on the cartridge needle holder may engage the second coupling member on the cartridge needle slider in a plane parallel to the needle axis such that the needle penetration forces in the perpendicular direction may deform the compliant coupling consisting of or located between the first and second coupling members. The forces in the perpendicular direction may be directed to a plane parallel to the needle axis and via the linear guide of the cartridge needle slider be effectively guided to the housing. The first coupling member may include a plurality of first coupling members (or first couplers or first coupling parts) to compensate for needle penetration forces directed in several directions that are all perpendicular to the insertion axis. The first coupling members may be circumferentially arranged around the cartridge needle holder engaging a plurality of second coupling members (or second couplers or second coupling parts) arranged on the cartridge needle slider. The cartridge needle holder may be arranged inside the cartridge needle slider, thus a plurality of first coupling members may radially extend outwards from the cartridge needle holder engaging a plurality of second coupling members that may extend radially inwards from the cartridge needle slider.

In certain implementations, the first coupling member and the second coupling member may elastically engage each other and/or may be in a linear or rotational friction fit engagement. When the two coupling members engage each other in a plane parallel to the needle axis then the elastic or frictional forces of the engagement may be configured to compensate the needle penetration forces when the compliant coupling is deformed by moving the first coupling member relative to the second coupling member or vice versa moving the second coupling member relative to the first coupling member. When the first and second coupling members are moved relative to another, then the position of the cartridge needle holder may change with respect to the cartridge needle slider as the compliant coupling is deformed. Therewith also the position of the part of the cartridge needle that is coupled to the cartridge needle holder may change during insertion. The engagement between the cartridge needle holder and the cartridge needle slider, via at least one pair of coupling members, may be an elastic engagement, a frictional engagement or a combination thereof. Optionally one or both of the coupling members may be plastically deformed after the elastic deformation. The change of position between the cartridge needle holder and the cartridge needle slider may be a movement perpendicular to the insertion axis, or the cartridge needle holder may rotate or tilt relative to the cartridge needle slider. Thus there are more options available for shaping and designing the compliant coupling by combining frictional, elastic or rotational force compensators. The relative movement between the cartridge needle holder with respect to the slider may trigger a signal, for example an acoustic signal. When the cartridge needle axis deviates too much from the insertion axis, this may be due to a failure and the acoustic signal may be a warning or alarm signal. Alternatively the relative movement between the slider and the holder may be tracked or followed by a sensor or an electrical contact may be established providing a visual (LED) or acoustic (vibration alarm) signal to the user that the device is, due to a bent needle, out of specification (e.g., non-compliant) and a health care professional should be contacted.

In further implementations, the first coupling member may include at least one protrusion radially extending from the cartridge needle holder whereby the protrusion may be at least partially elastically and/or plastically deformable and may engage at least one second coupling member shaped as a rigid surface on the cartridge needle slider. The second coupling member may be oriented parallel to the insertion axis. Alternatively at least one first coupling member may include a rigid protrusion radially extending from the cartridge needle holder engaging at least one second coupling member shaped as an at least partially elastically and/or plastically deformable surface on the cartridge needle slider. The second coupling member again being oriented parallel to the insertion axis in the alternative embodiment. A protrusion radially extending from the cartridge needle holder may not be limited to a single protrusion but may defines at least one protrusion. For instance, two protrusions, three protrusions, or four protrusions may be provided. The second coupling member is not restricted to a single second coupling member but may engage each of the first coupling members. Therefore two, three, or four second coupling members may be provided. The coupling members may form pairs and may ensure that the cartridge needle holder is held in a stable position with respect to the cartridge needle slider when in the first position. During movement of the cartridge needle slider from the first position towards the second position (when the cartridge needle has not penetrated yet the septum) then the at least one pair of coupling members may ensure that the cartridge needle holder remains in a stable position. Upon penetration of the septum, penetration forces perpendicular to the insertion axis and acting on the insertion needle may occur and then the first and second coupling members of at least one pair of coupling members may be moved relative to another such that the position of the cartridge needle holder shifts with respect to the cartridge needle slider as the compliant coupling is deformed. The relative movement of the first and second coupling members of at least one pair of coupling members may result in the aforementioned elastic deformation, friction or plastic deformation thereby compensating, absorbing or reducing the penetration forces perpendicular to the insertion axis.

The cartridge may include a barrel, optionally a glass barrel, defining a cartridge axis and the cartridge may be in a fixed position with respect to the housing and the cartridge axis may be aligned with the insertion axis when the cartridge needle slider is in the first position. The cartridge may be in a fixed position with respect to the housing and the device may be a prefilled device ("ready-to-use"), e.g., the cartridge may already be present in the device and may be ready to use such that the patient does not have to insert a cartridge in the device. Moving the cartridge in a device may lead to larger off-axis movements due to the relatively large dimensional tolerances of (glass) cartridges and movement over a longer distance, e.g., at least the length of the cartridge. By using a prefilled device, the alignment of the cartridge and the cartridge needle holder is not critical compared to a device requiring movement of the cartridge. In a prefilled device, the cartridge needle slider moves over a shorter distance for needle insertion and the parts of the slider, the coupling members and the housing may thus be made with high precision and low dimensional tolerances. Therefore the cartridge needle slider may be precisely aligned with the cartridge (and the septum). The alignment of the cartridge axis and the needle axis is an advantage for penetrating the septum in the septum's center such that the cartridge needle enters the center of the neck of the of the cartridge's barrel when penetrating the septum to establish a fluid connection between the medicament in the cartridge and the cartridge needle.

In some implementations, the assembly is not an alignment arrangement configured to align the cartridge axis and the insertion axis when the cartridge needle slider moves from the first position to the second position. An off-axis needle penetration, e.g., the needle axis being oblique to the insertion axis, may be allowed in the present disclosure resulting in needle penetration forces partially compensated for by a shift of the cartridge needle holder with respect to the cartridge needle slider but not fully aligning the needle axis to the insertion axis. Thus after insertion through the septum, the needle axis may still be oblique to the insertion axis. The assembly may be used in combination with prefilled devices or devices without moving the cartridge with respect to a fixed insertion needle. In some implementations, the cartridge needle slider and the cartridge needle holder may be coaxially arranged around the insertion axis when the cartridge needle slider is in the first position. The cartridge needle slider may be inserted into the cartridge needle holder and the coaxial arrangement may be beneficial for alignment of the parts during assembly.

The cartridge needle holder may be moved out of the coaxial arrangement with respect to the cartridge needle slider when the needle axis is not parallel to the insertion axis when the cartridge needle slider is moved into the second position thereby generating needle penetration forces perpendicular to the insertion axis deforming the compliant coupling. If the cartridge needle axis and the cartridge axis remain aligned or parallel during movement of the cartridge needle slider from the first position to the second position, then the septum will be penetrated perpendicular to, and in the center of the septum such that no off-axis penetration forces are generated. In both cases, needle penetration forces acting on the needle and directed along the insertion axis will occur, but those will not be compensated for, absorbed or reduced by the compliant coupling.

The cartridge needle holder may be axially fixed to the cartridge needle slider may allow movement with respect to the cartridge needle holder perpendicular to the insertion axis, or a pivoting or a rotational movement around the insertion axis against a bias or resistance of the compliant coupling. The cartridge needle slider may be linearly guided by the housing by a splined engagement defining the insertion axis.

The cartridge needle holder may be axially fixed when inserted into the cartridge needle slider to transfer the linear movement of the cartridge needle slider to the cartridge needle holder. The axial fixation may also ensure that the needle penetration forces directed parallel to, or along the insertion axis are compensated for or absorbed. Optionally a gearing mechanism, a motion link or a threaded engagement may transfer the linear motion of the cartridge needle slider to the cartridge needle holder with a defined transmission ratio. For instance, the cartridge needle holder may be axially fixed, for instance by stop surfaces on the cartridge needle slider and counter stop surface on the cartridge needle holder. When the cartridge needle slider is moved from the first to the second position the stop surface and counter stop surface may abut.

In some implementations, the cartridge needle in the assembly may be connected to the cartridge needle holder by an elastic member such as an elastic adhesive.

The cartridge needle slider may include the cartridge needle holder and the needle may be moved from the first to the second position by a driver, such as a spring for an efficient and fast insertion, for instance within milliseconds. The forces acting on the needle during penetration, which are oriented parallel to the insertion axis are guided to the cartridge needle holder and may damage the connection between them and therefore an elastic adhesive or member may be beneficial as it introduces an elastic member functioning as a shock absorber for the connection and thereby reduces the fracture risk for the connection due to needle penetration forces oriented along the insertion axis. The fracture risk may be higher if a rigid adhesive like a thermosetting epoxy or an acrylic based adhesive is used. Accordingly, a silicone based adhesive may be used, such as a medical grade adhesive according to USP Class VI or ISO 10993-5. The spring may be a compression spring, a leg spring or a spiral spring. As an alternative to a spring, the driver may include a biasing member or a gas driven power mechanism.

The driver in the assembly may be a spring located between the housing and the cartridge needle slider and may act on the housing and the cartridge needle slider, the spring being retained in a compressed state to provide a biasing force on the housing and the cartridge needle slider when the cartridge needle slider is held in the first position with respect to the housing by a releasable locking feature.

The cartridge needle insertion may be spring driven such that the user need not manually provide the force to penetrate the septum; and a spring may ensure that the septum can be penetrated at a high speed such that the septum is penetrated within milliseconds, such as below 10 milliseconds, or below 5 milliseconds. This in contrast to devices that are not prefilled, or where a cartridge is inserted manually and during insertion the septum is also penetrated by a cartridge needle that is fixed with respect to the housing. A knob on the cartridge needle slider may engage a locking feature, which may be shaped as a locking fork on a slider and the slider (e.g. a slider different from the cartridge needle slider) may be moved from a starting position where the locking fork engages the knob on the cartridge needle slider such that the cartridge needle slider may be held in the first position. The slider may be linearly guided by the housing (splined for example) and when the slider is moved, the engagement between the locking fork and the knob may be released such that the spring decompresses and moves the cartridge needle slider from the first to the second position. The linear guide of the slider with respect to the housing and the linear guide of the cartridge needle slider with respect to the housing may be oriented perpendicular to one another. The spring may be selected from a compression spring, a spiral spring, a cone-shaped spiral spring, a torsional spring or a leaf spring. Optionally, the linear guides may be lubricated to prevent blocking during movement and reduce the frictional losses.

The first coupling member may be hollow and may be part of, or form a passage for, a fluid conduit establishing a fluid link between a medicament present in the cartridge and the cartridge needle.

The fluid conduit may include several components, such as a flexible tube connecting the cartridge needle holder holding the cartridge needle on one end, and a skin needle holder holding a skin needle on the other end. The fluid conduit must be guided when the cartridge needle holder moves to the second position and/or when the skin needle is inserted into the patient's surface. Integrating the one of the first coupling members into the fluid conduit may be beneficial for fixing the fluid conduit (or tube) to the cartridge needle slider. This may reduce the number of parts required to assemble or fix the fluid conduit into the device as the cartridge needle holder may be snap fitted into the cartridge needle slider. For that purpose one of the first coupling members may be hollow allowing for fluid transport from the cartridge through the cartridge needle and via the cartridge needle holder having the hollow coupling member to the tubing and finally via the skin needle into the patient.

The cartridge needle may be a hollow needle whereby the tip of the needle is sharpened and may have a closed end such as a pencil tip needle or the tip of the needle is sharpened and may have an open end.

The tip of the needle may be sharpened to facilitate the penetration of the needle through the septum as the cartridge needle slider moves from the first position to the second position. The pencil tip needle may have a closed end at the tip and at least one opening in a side wall of the needle. As the pencil tip needle penetrates the septum of the cartridge, the sharp tip penetrates the septum without the risk of punching the septum resulting in coring and/or fragmentation (particles) of the septum potentially leading to needle clogging. A hollow tip of the needle may also sharpened and may punch the septum such that the end of the hollow needle may get blocked. The use of a pencil tip needle may increase the reliability of the device. The use of a compliant coupling in the present invention may reduce the risk of punching the septum and may decrease the risk of needle blocking if a hollow (or open) needle tip is used.

The cartridge needle holder may be snap-fitted into the cartridge needle slider. The snap fit connection may facilitate the assembly process of the cartridge needle holder into the cartridge needle slider. The snap fit connection may be formed by flexible arms, deformable hooks and other snap fitting means. For instance the snap fit connectors may be made from plastic and an integral part of the cartridge needle slider or the cartridge needle holder and made using injection molding of a plastic. For instance, the cartridge needle slider may be constructed from a stiff material such as a glass fiber reinforced polyamide, whereas the cartridge needle holder may be constructed from a polyester such as PBT or a medical grade cyclo olefinic copolymer (COC). Alternatively, the snap fit connection may be established using a third part such as a stamped metal part. In some cases, the snap fit connection may not be releasable, e.g., may be non-detachable.

A further implementation includes an injection device with the assembly for the cartridge needle insertion mentioned previously and the injection device may be a prefilled patch injection device including a skin adhesive surface and a skin needle configured to move from a needle retracted position in the housing to a needle inserted position at least partially outside of the housing after the cartridge needle slider has moved from the first position to the second position.

BRIEF DESCRIPTION OF THE DRAWINGS

The subject matter of the present disclosure is explained in more detail in the following text with reference to the disclosed implementations, which are illustrated in the attached drawings, in which:

FIG. 3 illustrates a control element which is engaged with the needle carrier;

FIG. 4 illustrates the control element disengaging the needle carrier;

FIGS. 20a', 20b' and 20c' illustrate schematic diagrams of force-displacement curves for the forces along (N), and forces perpendicular (Q) to the insertion axis for the cartridge needle insertion process of corresponding FIGS. 20a, 20b, and 20c;

FIGS. 21a, 21b, and 21c illustrate a cartridge needle insertion process, with the cartridge needle axis oblique to the insertion axis and the forces in the insertion direction (N) and perpendicular to the insertion direction (Q), where the needle tip penetrates a top surface of the septum (FIG. 21a); the needle tip penetrates through the septum (FIG. 21b); and the needle fully penetrates through the septum (FIG. 21c);

FIGS. 21a', 21b' and 21c' illustrate schematic diagrams of force-displacement curves for the forces along (N), and forces perpendicular (Q) to the insertion axis for the cartridge needle insertion process of corresponding FIGS. 21a, 21b, and 21c;

FIG. 21d illustrates a cross-section of the septum when the cartridge needle has been inserted with the cartridge needle axis oblique to the insertion axis without a compliant coupling;

FIGS. 22a, 22b, and 22c illustrate a cartridge needle insertion with a compliant coupling mechanism and cartridge needle axis oblique to the insertion axis and the forces in the insertion direction (N) and perpendicular to the insertion direction (Q), where the needle tip penetrates a top surface of the septum (FIG. 22a); the needle tip penetrates through the septum (FIG. 22b); and the needle fully penetrates through the septum (FIG. 22c);

FIGS. 22a', 22b' and 22c' illustrate schematic diagrams of force-displacement curves for the forces along (N), and forces perpendicular (Q) to the insertion axis for the cartridge needle insertion process of corresponding FIGS. 22a, 22b, and 22c;

FIG. 22d illustrates a cross-section of the septum when the cartridge needle has been inserted with the cartridge needle axis oblique to the insertion axis with a compliant coupling;

DETAILED DESCRIPTION

Definitions

Figure 1:
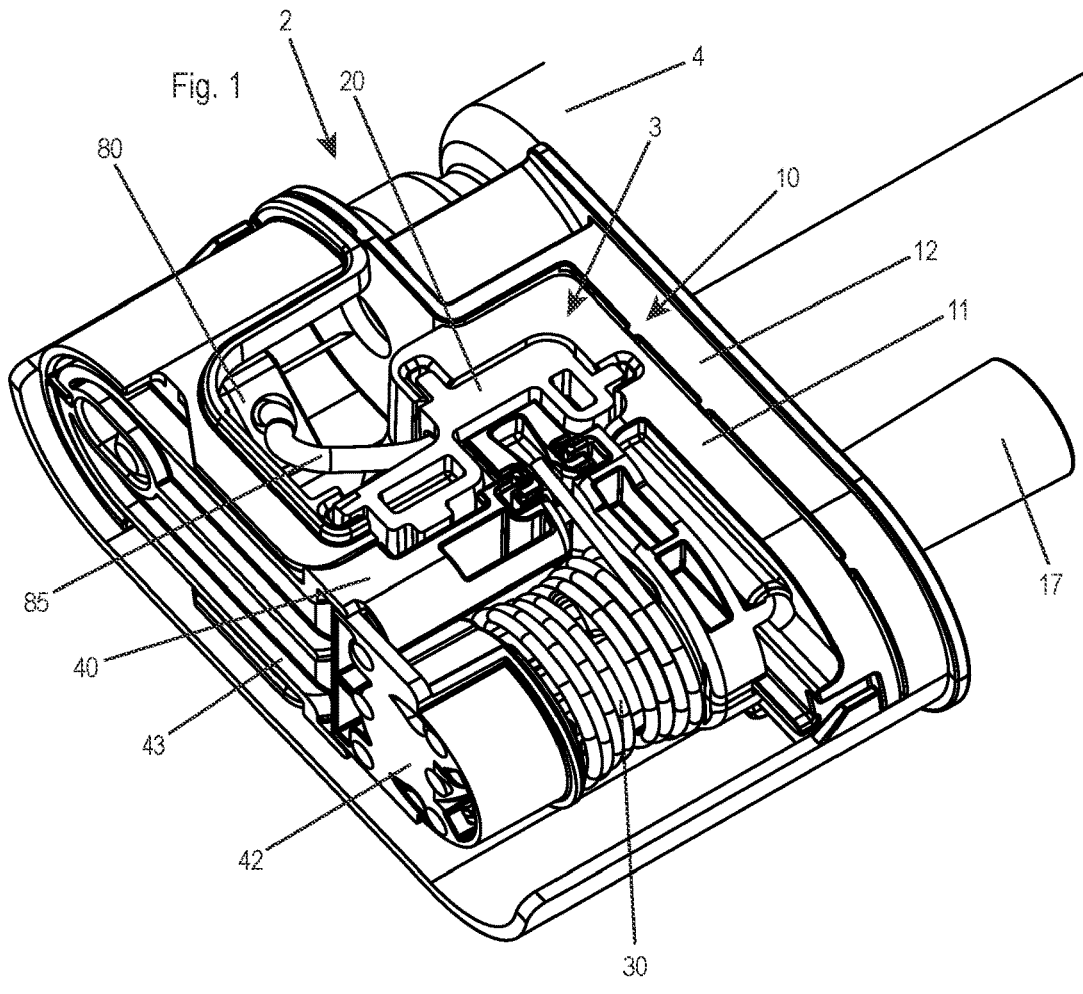
FIG. 1 illustrates an isometric view of a needle insertion and retraction module including a needle insertion and retraction mechanism, according to implementations of the present disclosure.

In the present disclosure, the terms "substance", "drug", "medicament" and "medication" are to be understood to include any flowable medical formulation suitable for controlled administration through means such as, for example, a cannula or a hollow needle, and includes a liquid, a solution, a gel or a fine suspension containing one or more medical active ingredients. A medicament can be a composition including a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

The term "distal" is meant to refer to the direction or the end of the drug delivery device carrying an infusion set, an injection needle or an injection cannula, whereas the term "proximal" is meant to refer to the opposite direction or end pointing away from the needle or cannula.

The term "injection system" or "injector" refers to a device that is removed from the injection site after each medication event or drug delivery process, whereas the term "infusion system" refers to a device with a cannula or needle that remains in the skin of the patient for a prolonged period of time, for example, several hours. An "on body delivery system" where a certain volume, a "bolus" is injected, is an injection system. An "on body delivery system" where a medicament is delivered at a certain delivery rate, for example a basal rate, is an infusion system.

In the claims, the word "comprising" does not exclude other elements or steps, and the indefinite article "a" or "an" does not exclude a plurality. For example "a first coupling" does not exclude the fact that there may be two "first coupling members" that functionally or structurally fulfill the purpose of "a first coupling member". The mere fact that certain elements or steps are recited in distinct claims shall not preclude the existence of further meaningful combinations of these elements or steps.

The term "penetration forces" are forces acting on the insertion needle during insertion of the needle along an insertion axis into a septum. The forces may be oriented parallel to an insertion direction defining an insertion axis for the insertion needle, or the forces, or a resultant component of the forces may be directed perpendicular to the insertion axis. The latter forces may also be called "off-axis" penetration forces. The penetration forces act on the needle or on a part directly coupled thereto, for example a needle holder, or alternatively the penetration forces act on a part indirectly coupled to the needle, for example a cartridge needle slider or a housing.

Referring to FIGS. 1 to 19 an embodiment is provided of Applicant's co-pending, commonly owned U.S. patent application having Ser. No. 17/149,347 and published as US 20210138151 A1, which provides a needle insertion and retraction module 2 including a needle insertion and retraction mechanism 3, but without a compliant coupling mechanism between a cartridge needle holder and cartridge needle slider as provided by the present disclosure. US 20210138151 A1 is incorporated herein in its entirety for any useful purpose.

As displayed in FIG. 1 the needle insertion and retraction mechanism 3 includes a housing 10 which is a multiple component housing. Particularly the housing 10 includes a first housing 11 and a second housing 12 which are connected to each other by positive fit or by firmly bonding or welding. Alternatively the first and the second housings 11, 12 are molded as a single part.

Figure 2:
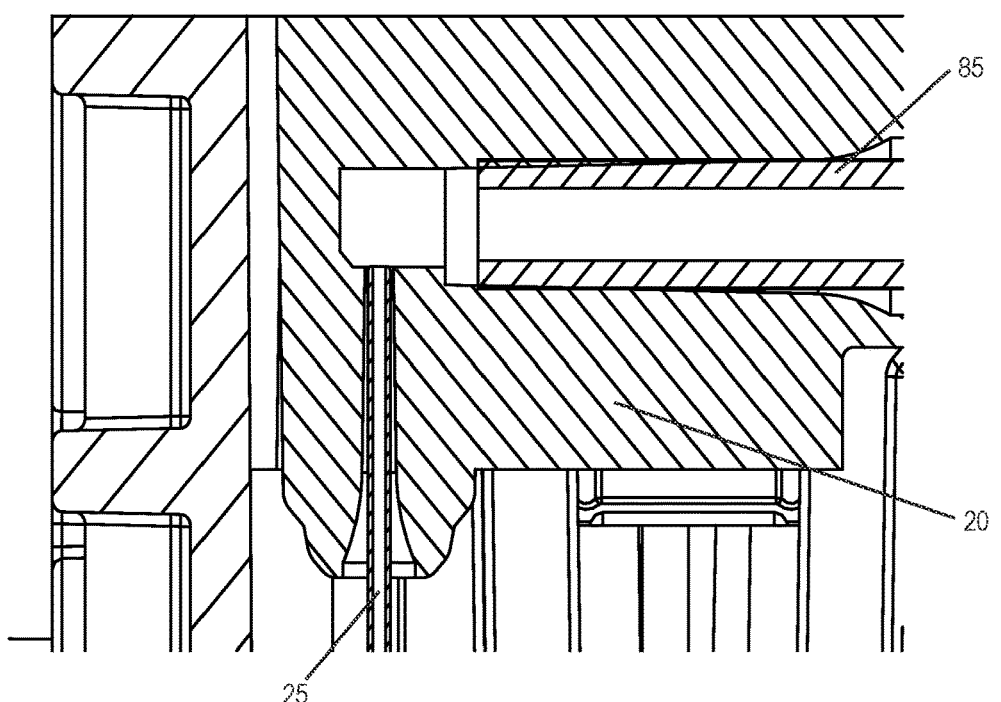
FIG. 2 illustrates a cross-sectional view particularly through a needle carrier.

The needle insertion and retraction mechanism 3 includes a needle carrier 20 which holds a needle 25 for insertion into the skin (FIG. 2) and which is linearly guided by the housing 10, particularly by the first housing 11. The housing 10 or the first housing 11 includes a longitudinal guide (FIG. 1) which engages the needle carrier 20 such that it is movable along the longitudinal axis of the needle 25. The longitudinal guide includes at least a first longitudinal groove and a second longitudinal groove formed by the housing 11. The needle carrier 20 includes at least a first rib and a second rib wherein the first rib engages the first groove and the second rib engages the second groove. Thereby the needle carrier 20 is linearly guided to be moved along the longitudinal axis of the needle 25. The needle carrier 20 is movable between an initial position (FIG. 1) in which the needle 25 which protrudes from the needle carrier 20 in a needle insertion direction is completely encompassed by the housing, and a needle insertion position (FIGS. 6 and 7) in which the needle protrudes from an outer surface of the housing, particularly the surface which is intended to be contacted or adhered to the skin of a patient. The housing 10 may include an opening or a pierceable wall through which the needle 25 is moved when the needle carrier 20 is moved from its initial position to its needle insertion position. The longitudinal axis of the needle 25 is substantially perpendicular or normal with respect to the surface which is intended to be adhered to the skin of the patient. The needle 25 is a hollow needle through which a medication or a medicament can be injected into the patient. The housing 10, particularly the housing 12 is adapted to retain a product container 4. In the example shown, the product container 4 is a cartridge, with a pierceable septum 5 (wall) at its forward end. The medicament of the cartridge 4 can be expelled through a flexible tube 85 which is in fluid communication with the hollow needle 25 and through the needle 25 in a patient. As can be seen in FIG. 2 the needle carrier 20 includes a channel which connects an end of the flexible tube 85 and the hollow needle 25 in a fluid guiding manner. The needle 25 is fixedly retained in a bore of the needle carrier 20. One end of the flexible tube 85 is fixedly retained in a bore of the needle carrier 20.

The other end of the flexible tube 85 is fixedly retained in a bore of a needle carrier 80 (or so-called cartridge needle carrier) which connects a hollow needle 70 (or cartridge needle) in a fluid guiding manner with the flexible tube 85, by means of a channel formed by the needle carrier 80 (see, e.g., FIGS. 1 and 8 to 10). The needle 70 is fixedly retained in a bore of the needle carrier 80. One end of the flexible tube 85 is also fixedly retained in a bore of the needle carrier 80.

Figure 13:
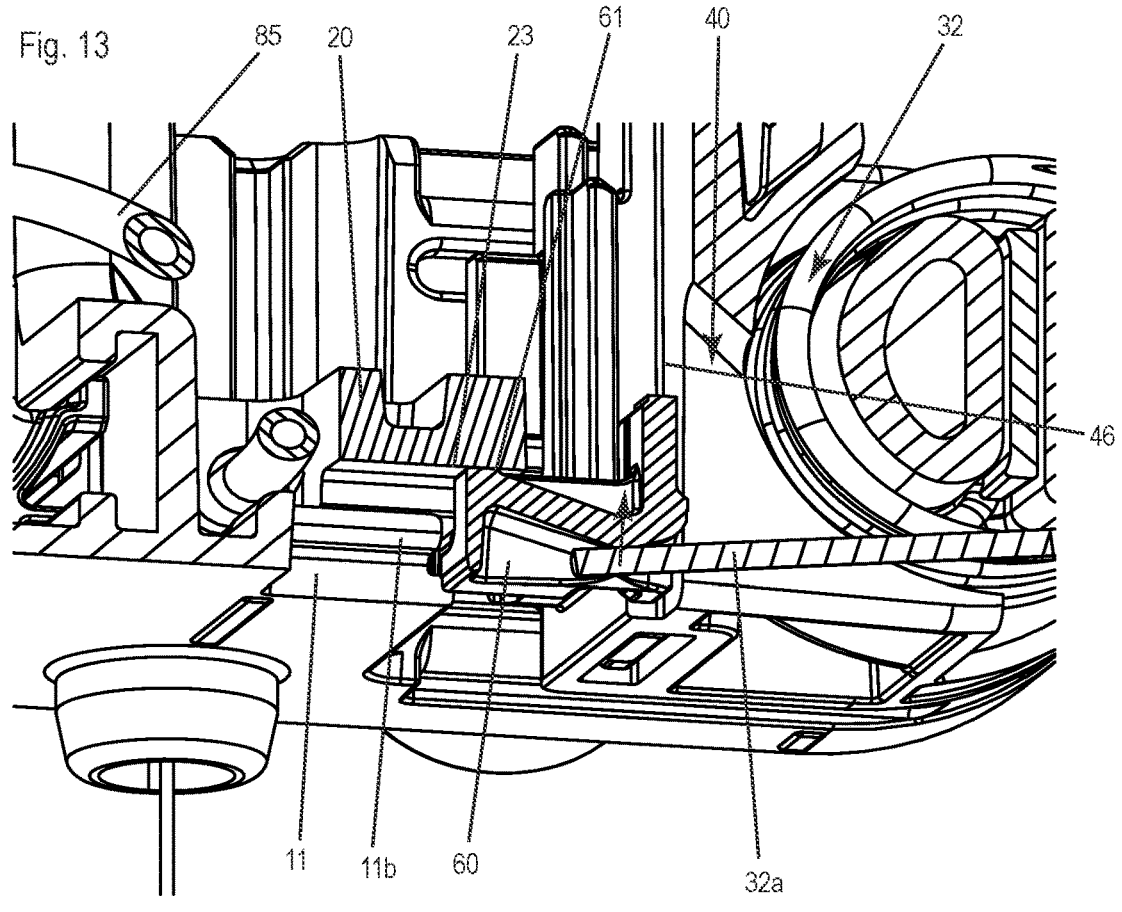
FIG. 13 illustrates a second intermediate member between a second spring arm and the needle carrier, where the intermediate member is disengaged from the housing and engaged with the needle carrier.

The needle insertion and retraction mechanism 3 further includes a first spring member 31 which is adapted to move the needle carrier 20 with respect to the housing 10 in a needle insertion direction along the longitudinal axis of the needle 25 (see, e.g., FIGS. 5 to 8). Furthermore, a second spring member 32 is provided which is adapted to retract the needle carrier 20 with respect to the housing 10 in a needle retraction direction, which is opposed to the needle insertion direction (FIG. 13). In the embodiment shown, the first spring member 31 and the second spring member 32 are integrally formed by one spring 30 (FIG. 1). However, in an alternative, spring members 31 and 32 can be separate from one another.

Figures 7, 8:
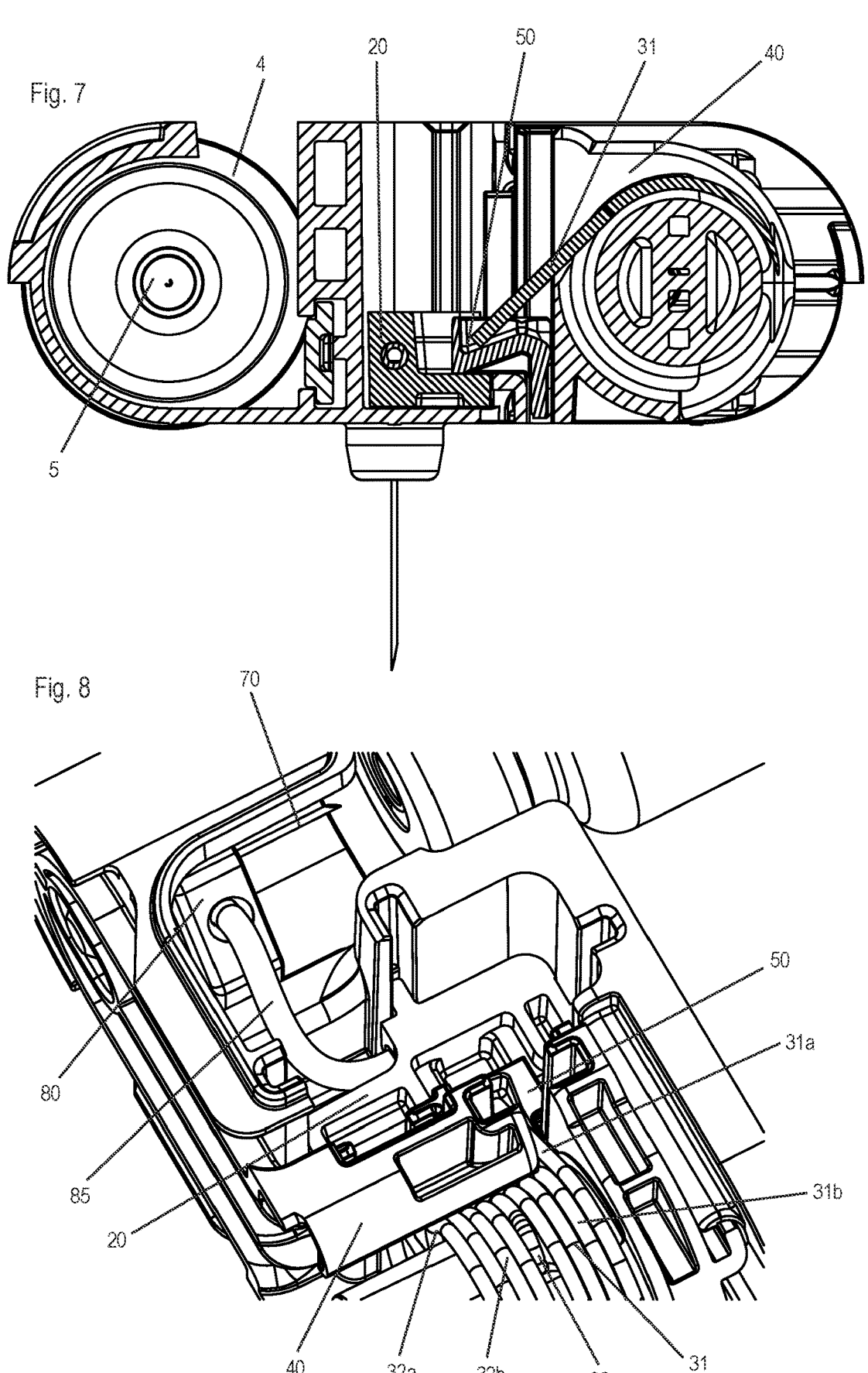
FIG. 7 illustrates a further view of the needle carrier in a needle insertion position.
FIG. 8 illustrates a cartridge needle carrier with a cartridge needle (e.g., spike) in a first position.

The first spring member 31 includes a first helical spring section 31*b* which operates as a torsion spring (FIG. 8). A first arm 31*a* protrudes from the circumference of the first helical spring section 31*b*. The first spring member 31 is supported on a control element 40, preferably shaped as a slider, such that the first helical spring section 31*b* can be strained or tensioned by pivoting the arm 31*a*. Furthermore, the energy stored in the first helical spring section 31*b* can be released such that the first arm 31*a* is pivoted in a direction which causes the needle carrier 20 to move in the needle insertion direction.

The second spring member 32 (FIG. 13) includes a second helical spring section 32*b* which operates as a torsion spring. A second arm 32*a* protrudes from circumference of the second helical spring section 32*b*. The second spring member 32 is supported on the control element 40 or slider such that the second helical spring section 32*b* can be strained or tensioned by pivoting the second arm 32*a*. Furthermore, the energy stored in the second helical spring section 32*b* can be released whereby the second arm 32*a* is pivoted.

The first helical spring section 31*b* and the second helical spring section 32*b* surround a portion of the control element 40. This portion includes a slit which retains an interconnecting section 33 of the spring 30 which interconnects the first helical spring section 31*b* and the second helical spring section 32*b* and which also provides the support section of the first spring member 31 and the second spring member 32 for tensioning the spring sections 31*a* and 31*b*. In embodiments with two separate spring members 31 and 32 each of them may include a supporting section by which the spring member 31, 32 is supported on the control element 40.

Figures 16, 17:
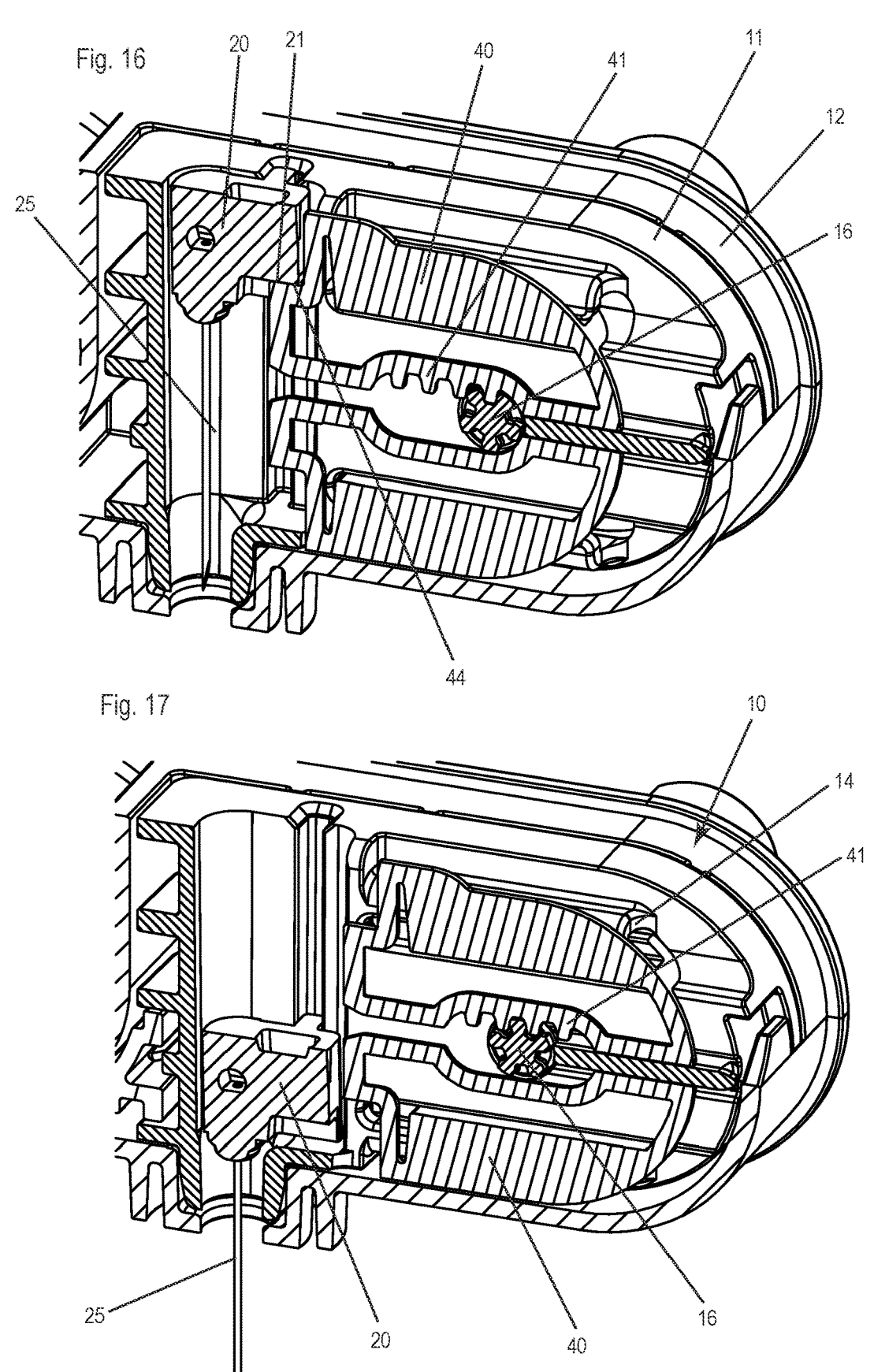
FIG. 16 illustrates a control element in its starting position.
FIG. 17 illustrates a control element which has been moved in the needle release position.
Figure 18:
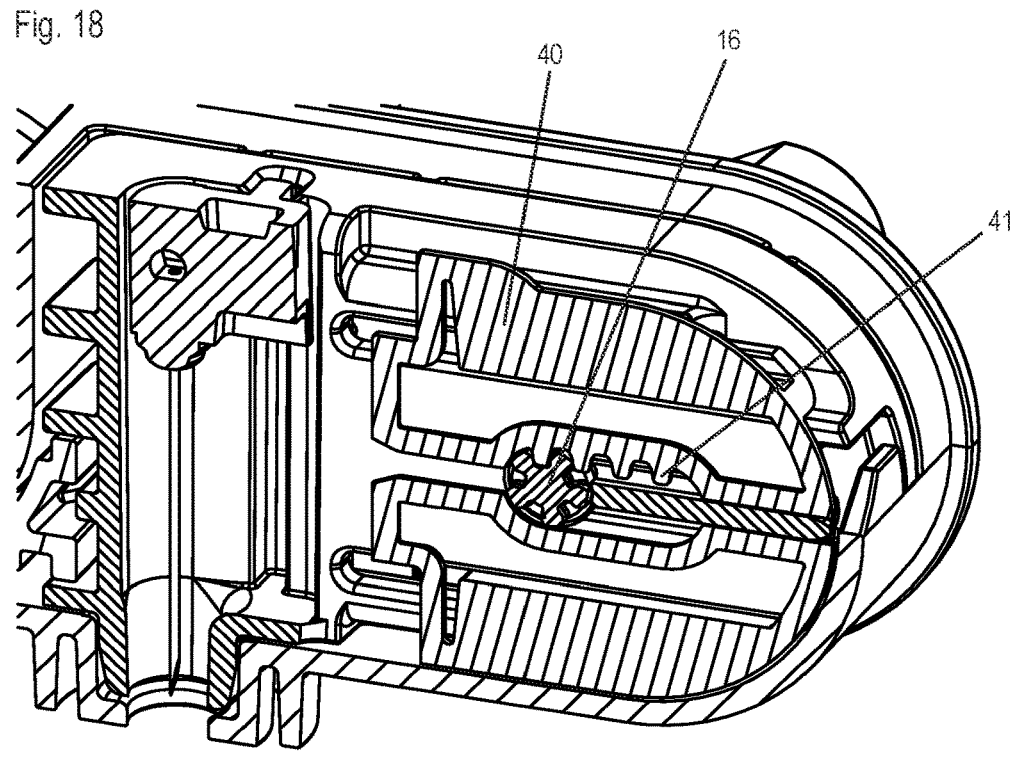
FIG. 18 illustrates the control element which has been moved in its needle retraction position.
Figure 19:
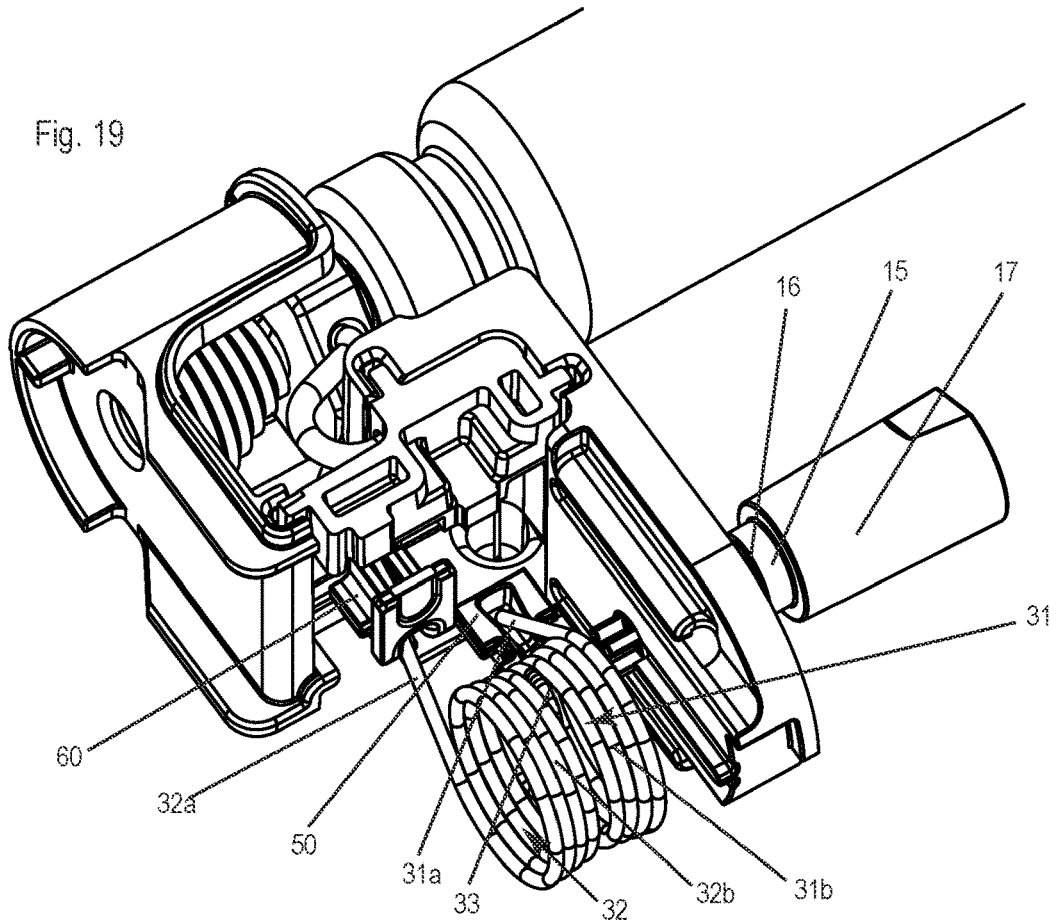
FIG. 19 illustrates a spring for moving the needle carrier in the needle insertion direction and in the needle retraction direction.

The control element 40, preferably the slider, is linearly guided via linear guide 14 with respect to the housing 10 to be moved transversely with respect to the longitudinal axis of the needle 25. The control element 40 can be moved from a first position or starting position (FIG. 16) to a second position or needle insertion release position (FIG. 17). The slider may be moved to a third position, a so-called needle retraction release position (FIG. 18). The control element 40 moves from the starting position to the needle retraction release position, including the positions between the starting position and the needle retraction release position, in the same direction. The spring 30 or the spring members 31, 32 are attached to the control element 40 such that they move together with the control element 40. The needle insertion and retraction mechanism 3 or module 2 provides for a drive shaft 15 which is rotatably guided by the housing 10, e.g. by virtue of a rotational bearing (FIG. 19). The drive shaft 15 is operatively connected to the control element 40. The drive shaft 15 and the control element 40 are adapted to cooperate with each other such that rotation of the drive shaft 15 in a first rotational direction causes the control element 40 to be linearly moved, namely transversely with respect to the longitudinal axis of the needle 25 because of the linear guide provided by the housing 10.

The drive shaft 15 includes a gear wheel 16 (FIGS. 16 to 18) which is formed by or connected to the drive shaft 15 and which engages a gear rack 41 formed by or connected to the control element 40 to form a rack-and-pinion arrangement. By rotating the drive shaft 15 or the gear wheel 16 the control element 40 is linearly moved.

The drive shaft 15 includes a coupling member 17 which is adapted to be coupled with a coupling member of a drive shaft of a drive mechanism (not shown). Thereby, rotation of the drive shaft 15 of the drive mechanism in a first direction is transmitted to the drive shaft 15 in the first direction causing the control element 40 to be moved in the first longitudinal direction. The drive shaft 15 is rotated by an active drive, either directly or via a gearing arrangement that may include a worm wheel.

Figure 5:
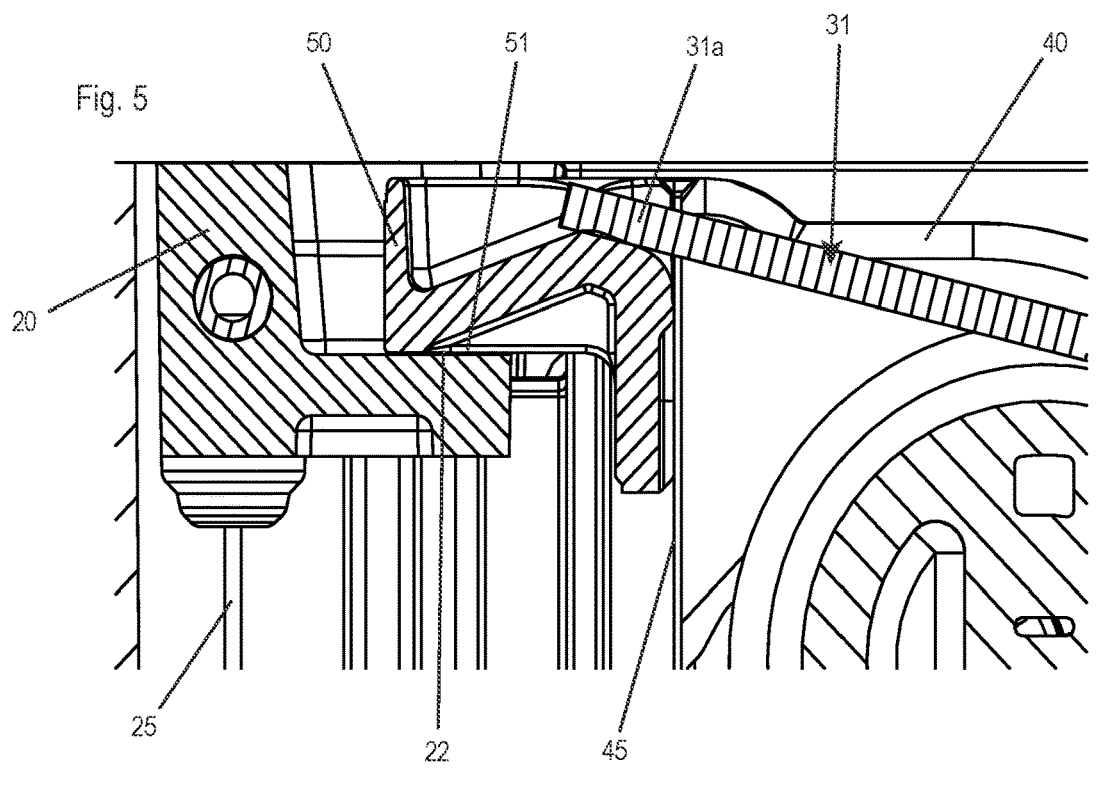
FIG. 5 illustrates a first intermediate member between a spring arm and a needle carrier with the needle carrier in a needle retracted position.
Figure 6:
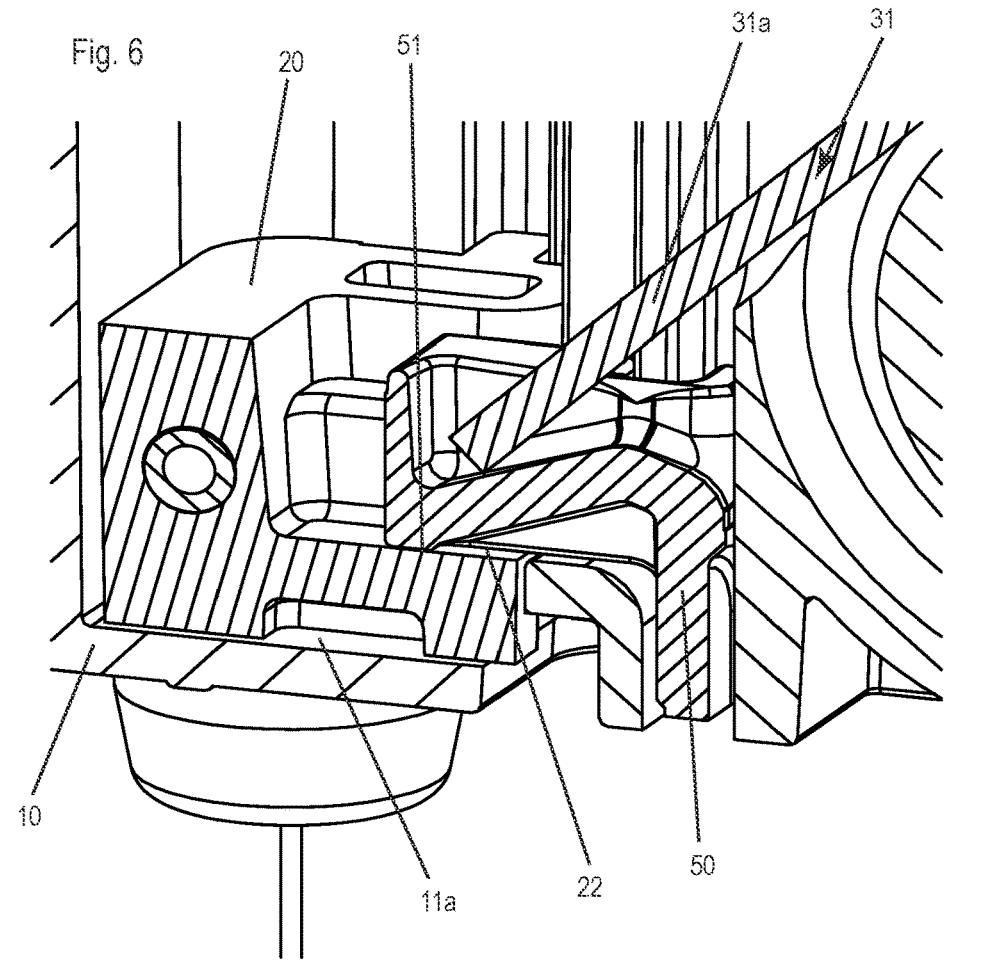
FIG. 6 illustrates the parts of FIG. 5 with the needle carrier in a needle insertion position.

The control element 40 includes a cap 42 which is connected to a main body 43 of the control element 40 (FIG. 1). The cap 42 is connected to or partially fits over the portion which is surrounded by the helical spring sections 31*b*, 32*b*. The cap 42 keeps the spring 30 or the spring members 31, 32 in position on the control element 40 or the main body 43 (FIG. 1). The control element 40 is operatively coupled to the needle carrier 20 to prevent the needle carrier 20 from being moved in the needle insertion direction when the control element 40 (or slider) is in its starting position (FIG. 3). As can be seen in FIG. 3, the control element 40 or its main body 43 includes a stop surface 44 on which a counter stop surface 21 of the needle carrier 20 rests when the control element 40 is in its starting position. The needle carrier 20 is thereby prevented from being moved in the needle insertion direction. As can be seen in FIG. 4, the stop surface 44 disengages from the counter stop surface 21 when the control element 40 is moved by the rack-and-pinion arrangement in its insertion release position such that the needle carrier 20 is free to be moved in the needle insertion direction. The first arm 31*a* or more generally the spring member 31 operates on the needle carrier 20 via a first intermediate member 50 (FIG. 5) to drive the needle carrier 20 from the initial position (FIG. 5) in the needle insertion direction into a needle insertion position (FIG. 6).

A first intermediate member 50 includes a counter stop surface 51 which engages a stop surface 22 of the needle carrier 20 when the control element 40 is in its starting position and/or in its insertion release position. The first spring member 31 applies a spring force on the first intermediate member 50 which in turn transmits the spring force to the needle carrier 20 as long as the first intermediate member 50 and the needle carrier 20 are in engagement. A spring powered movement of the needle carrier 20 in the needle insertion direction, when the control element 40 is in its starting position, is prevented when stop surface 44 and counter stop surface 21 are engaged (FIG. 3). As soon as the control element 40 and the needle carrier 20 are disengaged, the first spring member 31 drives the needle carrier 20 in the needle insertion direction until the needle carrier 20 abuts an axial stop 11*a* provided by the housing 10, particularly by the first housing 11, in the needle insertion position of the needle carrier 20. The control element 40 includes a linear guide 45 which is adapted to linearly guide the first intermediate member 50 in the direction of the longitudinal axis of the needle 25 or the needle insertion and retraction direction (FIG. 5). The linear guide 45 causes the first intermediate member 50 to be moved together with the control element 40 transversely with respect to the longitudinal axis of the needle from the starting position via at least the needle insertion release position to the needle retraction release position. By moving the control element 40 (or slider) from its starting position to its needle insertion release position, the first intermediate member 50 is moved with respect to the needle carrier 20 but does not yet disengage from the needle carrier 20. That is to say that the first intermediate member 50 and the needle carrier 20 remain engaged in the needle insertion release position of the control element 40.

Figure 12:
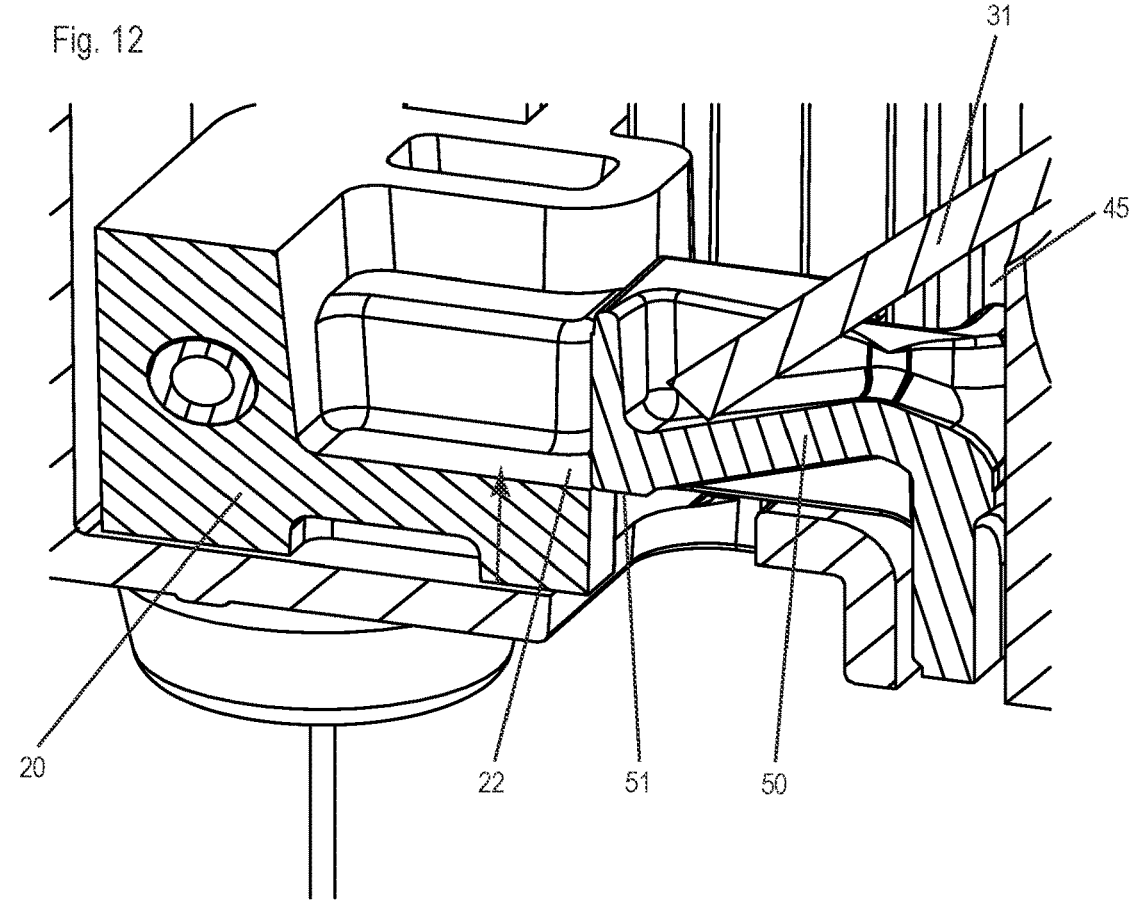
FIG. 12 illustrates the first intermediate member disengaged from the needle carrier.

When the control element 40 is moved further from the second slider position by activating the rack and pinion arrangement to its retraction release position (third slider position), the second spring member 32 is operatively coupled to the needle carrier 20 such that the second spring member 32 drives the needle carrier 20 in the needle retraction direction. By moving the control member 40 into the needle retraction release position, the first intermediate member 50 and the needle carrier 20, particularly the stop surface 22 and the counter stop surface 51, disengage since the first intermediate member 50 is moved together with the control element 40 transversely with respect to the longitudinal axis of the needle 25. The needle carrier 20 is now free to be moved in the needle retraction direction which is opposed to the needle insertion direction (FIG. 12).

For example, when the first intermediate member 50 is disengaged from the needle carrier 20, it—driven by the remainder of the spring force of the first spring member 31—abuts a stop formed by the control element 40, particularly by the end of the linear guide 45. Thereby, the remainder of the spring force of the first spring member 31 advantageously prevented from interfering with the further operation of the mechanism.

A second intermediate member 60 (FIG. 13) is provided, which is linearly guided by the control element 40 in the needle retraction direction, e.g., by a linear guide 46 provided by the control element 40. The linear guide 46 is adapted such that the second intermediate member 60 is linearly movable with respect to the control element 40 along the longitudinal axis of the needle 25 or in the needle retraction direction. Furthermore, the linear guide 46 causes the second intermediate member 60 to be moved together with the control element 40 transversely with respect to the needle retraction direction or transversely with respect to the longitudinal axis of the needle 25.

Figure 14:
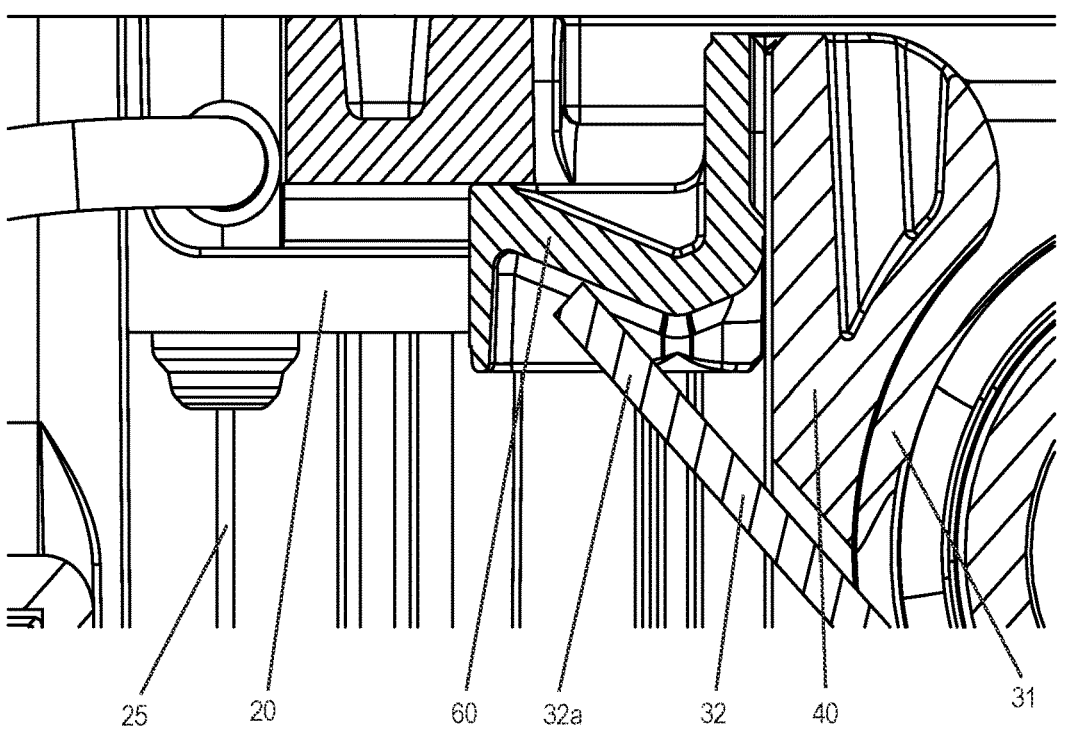
FIG. 14 illustrates the needle carrier which has been moved in the retracted position.
Figure 15:
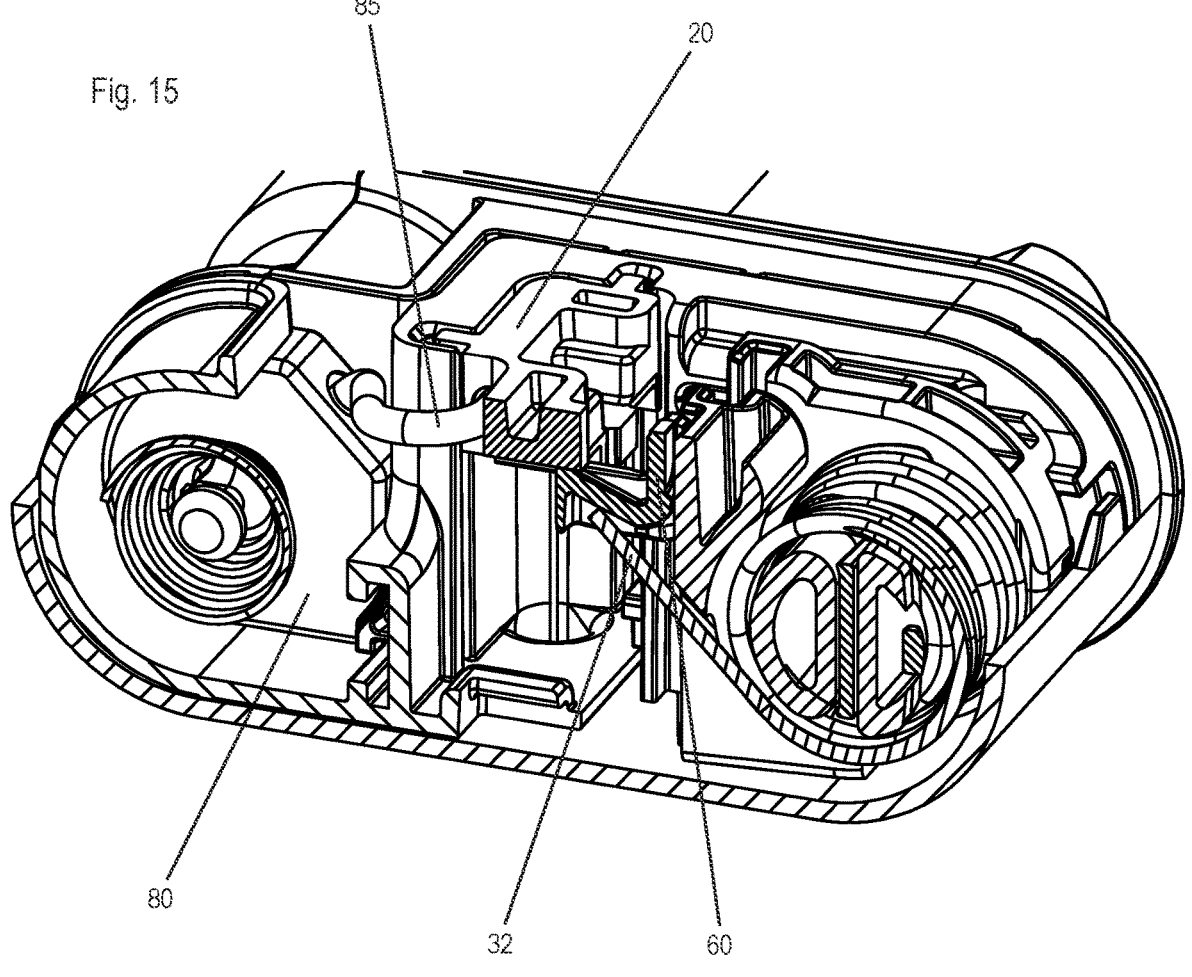
FIG. 15 illustrates a perspective view of the needle carrier which has been moved in the retracted position.

When the control element 40 is in its starting position (first slider position) and/or in its insertion release position (second slider position), the second intermediate member 60 it is engaged with the housing 10, particularly the housing 11, such that the second intermediate member 60 is prevented from being moved in the needle retraction direction (FIG. 13). The housing 10 includes a stop surface 11*b* with which the second intermediate member 60 is engaged to prevent the second intermediate member 60 from being moved in the needle retraction direction. The second spring member 32 applies a spring force on the second intermediate member 60 in the needle retraction direction. By moving the control element 40 in its retraction release position the second intermediate member 60 is disengaged from the housing 10, particularly from the stop surface 11*b*. Furthermore, the second intermediate member 60 or a counter stop surface 61 thereof engages with the needle carrier 20 or a stop surface 23 thereof. Thereby, the second intermediate member 60 and the needle carrier 20 are moved in the needle retraction direction driven by the second spring member 32 (FIG. 13). Thereby the needle carrier 20 is moved in its retracted position such that the needle 25 is completely retracted into the housing 10 (FIGS. 14 and 15).

To prevent the first intermediate member 50 and the second intermediate member 60 from interfering with each other, they are positioned offset from one another particularly in the direction which is transverse with respect to the longitudinal axis of the needle 25 (FIG. 19).

The first spring arm 31*a* rests on a convexly curved contact surface of the first intermediate member 50 as can be seen in FIG. 5. During, for instance needle insertion, the first intermediate member 50 is driven by the first spring member 31 in the needle insertion direction, the spring arm 31*a*, particularly its circumference surface, moves over the apex of the convexly curved contact surface, thereby the first arm 31*a* (or its circumference surface) particularly slides and/or rolls over the convexly curved contact surface. This arrangement reduces friction and/or reduces the risk of malfunction with respect to other arrangements.

Movement of the needle carrier 20 in the needle retraction direction is prevented at least by the remainder of the spring force of the first spring member 31 operating on the first intermediate member 50 as long as the first intermediate member 50 is engaged with the needle carrier 20 (FIG. 6).

Furthermore, as shown in FIG. 6, the free end of the first spring arm 31*a* includes an edge, for example, formed between the circumference surface and the end face of the first spring arm 31*a*. When the needle carrier 20 is in its needle insertion position, the edge contacts or rests on, particularly—to small or microscopically extent—grooves into, the first intermediate member 50, e.g., on an inclined surface thereof. The edge contacting or even grooving into the first intermediate member 50 increases friction between the first intermediate member 50 and the first spring arm 31*a*. Thereby, movement of the needle carrier 20 in the needle retraction direction is—in addition to the remainder of the spring force of the first spring member 31—made more difficult or even prevented as long as the first intermediate member 50 is engaged with the needle carrier 20. The angle between the inclined surface and the circumference surface may, for example, be smaller than the angle between the end face and the circumference surface.

The second spring arm 32*a* rests on a convexly curved contact surface of the second intermediate member 60 as can be seen in FIGS. 13 and 14. While the second intermediate member 60 is driven by the second spring member 32 in the needle retraction direction, the spring arm 32*a* moves over the apex of the convexly curved contact surface thereby the second arm 32*a* particularly slides and/or rolls over the convexly curved contact surface. This arrangement reduces friction and/or reduces the risk of malfunction with respect to other arrangements.

Movement of the needle carrier 20 back in the needle insertion direction is prevented at least by the remainder of the spring force of the second spring member 32 operating on the second intermediate member 60 as long as the second intermediate member 60 is engaged with the needle carrier 20 (FIG. 14).

Furthermore, as shown in FIG. 14, the free end of the second spring arm 32a includes an edge, for example, formed between the circumferential surface and the end face of the second spring arm 32a. When the needle carrier 20 is in its needle retraction position, the edge contacts or rests on, particularly—to small or microscopically extent—grooves into, the second intermediate member 60, e.g., on an inclined surface thereof. The edge contacting or even grooving into the second intermediate member 60 increases friction between the second intermediate member 60 and the second spring arm 32a. Thereby, movement of the needle carrier 20 back in the needle insertion direction is—in addition to the remainder of the spring force of the second spring member 32—made more difficult or even prevented as long as the second intermediate member 60 is engaged with the needle carrier 20. The angle between the inclined surface and the circumference surface may, for example, be smaller than the angle between the end face and the circumference surface.

Figure 9:
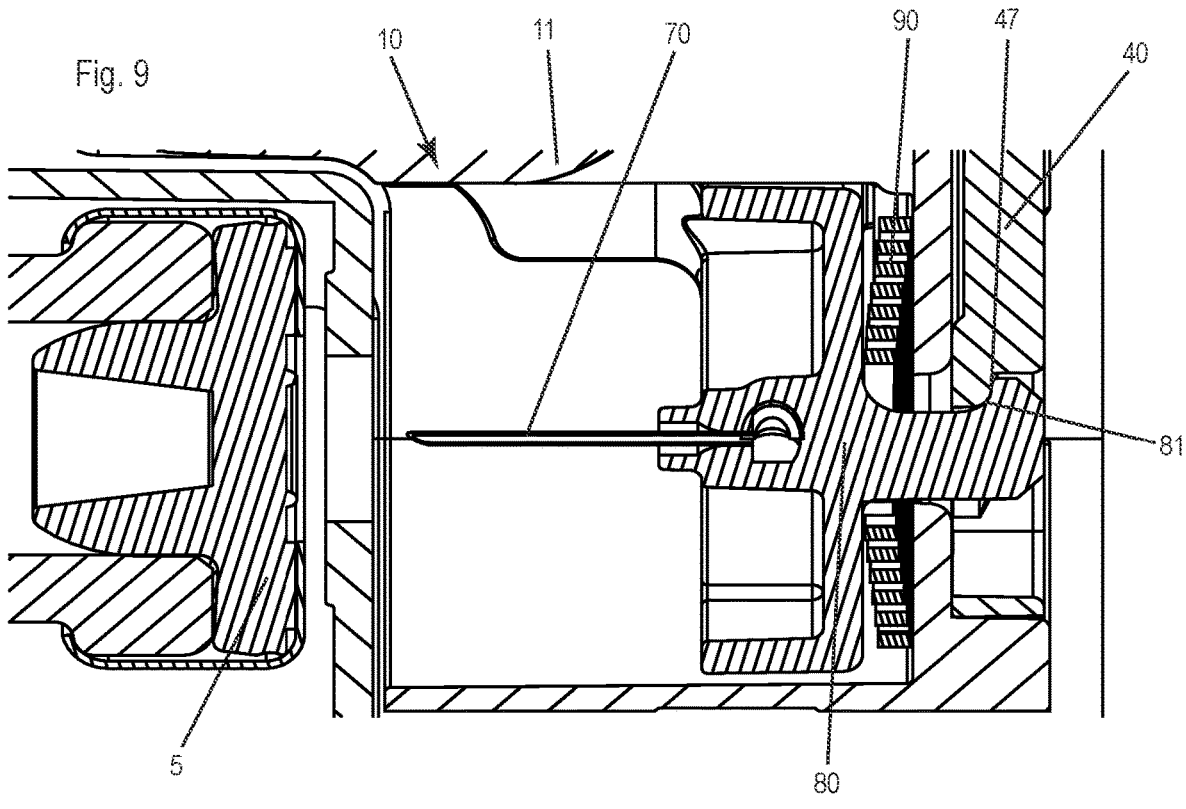
FIG. 9 illustrates a cross-sectional view of the cartridge needle carrier in a first position.
Figure 10:
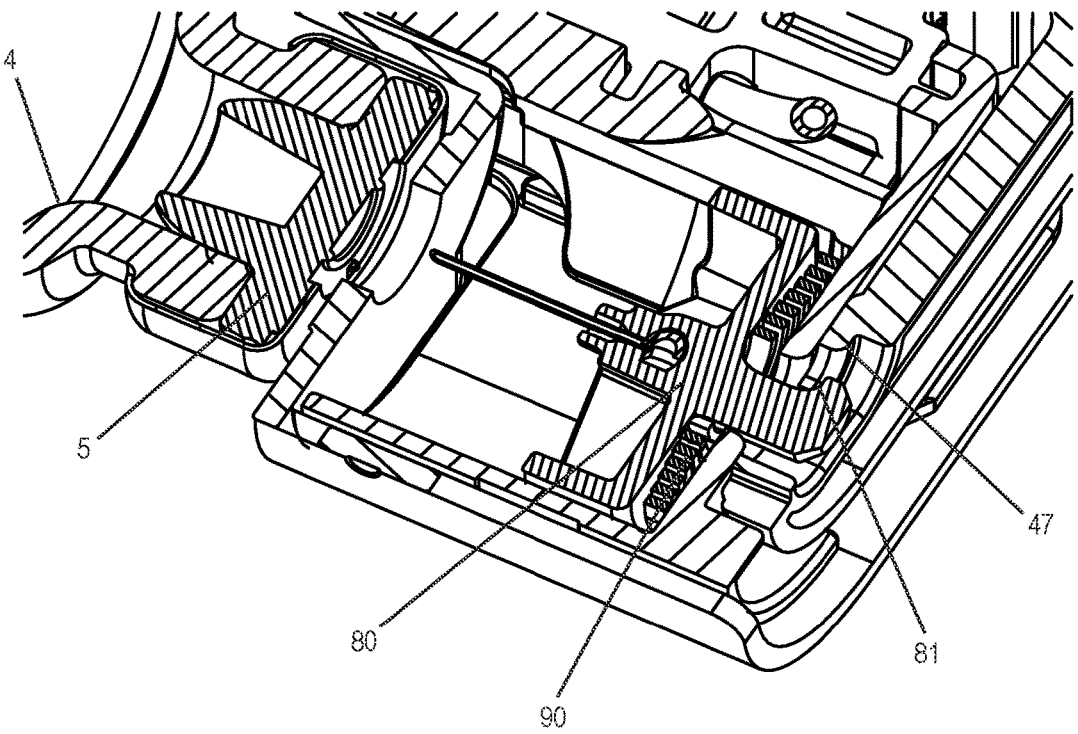
FIG. 10 illustrates a cross-sectional view of the cartridge needle carrier being released to be subsequently moved in a second position.

The needle carrier 80 holds a hollow needle 70 which may be also called a cartridge needle, which protrudes from the needle carrier 80 towards a receptacle for the product container (cartridge holder) or to a pierceable wall or septum 5 of the cartridge 4 (FIGS. 8 to 11). In FIGS. 9 and 10 the needle carrier 80 is in a first position in which the needle 70 does not pierce the septum 5 of the product container 4. The needle carrier 80 is linearly guided, e.g., by a linear guide provided by the housing 10, preferably by the housing 11, such that the needle carrier 80 can be moved linearly from a first position to a second position together with the needle 70. The movement from the first to the second position is along an insertion axis. By moving the needle carrier 80 from the first position to the second position the needle 70 pierces the septum 5 of the product container 4 such that needle 70 establishes a fluid communication between the medication inside the product container 4 and the needle 25. A spring 90 is provided, which may operates on the needle carrier 80 as a driver to drive the needle carrier 80 from the first position to the second position. In the first position of the needle carrier 80 the spring 90 is in a pre-tensioned condition. A variety of spring designs may be conceivable, whereby a conical helical spring 90 is preferred. One end of the spring 90 is supported on the needle carrier 80 and the other end of the spring 90 is supported on the housing 10, particularly the housing 11.

Figure 11:
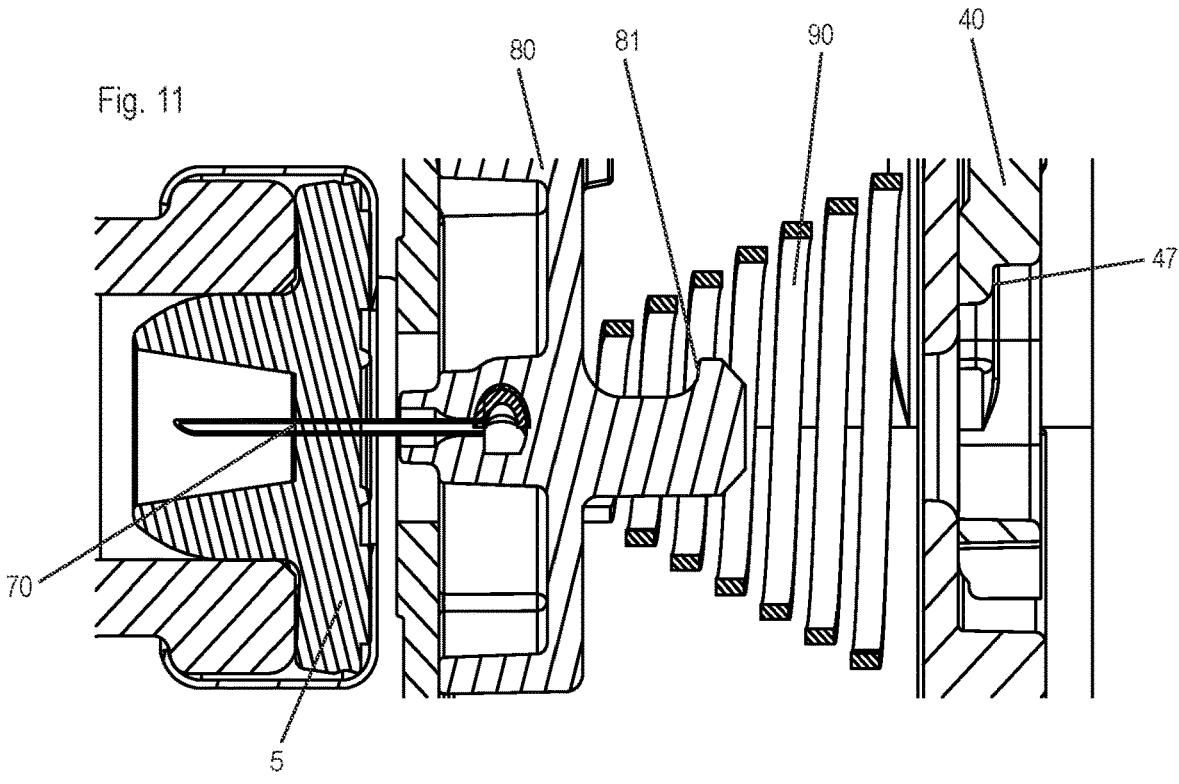
FIG. 11 illustrates a cross-sectional view of the cartridge needle carrier in a second position.

The control element 40 is engaged with the needle carrier 80, when the control element 40 is in its starting position. Thereby, the needle carrier 80 is retained in its first position and the spring 90 is prevented from expanding. Particularly, the control element 40 includes a retaining surface 47 which engages a counter surface 81 to prevent the needle carrier 80 from being moved from the first position to the second position. By moving the control element 40 (or slider) from its starting position in the first direction, e.g., the direction to the injection release position, the control element 40 is disengaged from the needle carrier 80, particularly the retaining surface 47 disengages from the counter surface 81 such that the needle carrier 80 is free to be moved from the first position to the second position (FIG. 10). The spring 90 expands and thereby drives the needle carrier 80 from the first position into the second position (FIG. 11). The needle insertion and retraction mechanism 3 can be adapted such that the needle carrier 80 is released before, after or at the same time the needle carrier 20 is released to be moved in the needle insertion direction.

The needle carrier 80 includes a main body which holds the needle 70 (or cartridge needle) and which is linearly guided by the housing 10. The cartridge needle may be a hollow steel needle or made from a suitable plastic material. A hollow steel needle may be affixed, e.g., glued or otherwise adhered, into the needle carrier 80. The needle carrier 80 includes a protrusion which protrudes from the main body opposite to the direction in which the needle 70 protrudes. The protrusion extends through the (conical) helical spring 90, through a section of the housing 10. The section of the housing 10 can be arranged between the section of the control element 40 which includes the retaining surface 47, and the needle carrier 80. The protrusion includes the counter surface 81.

FIGS. 20a-20d show a cartridge needle insertion process with the cartridge needle axis 53 parallel to the insertion axis 52 using a cartridge needle insertion mechanism and corresponding schematic diagrams 20a'-20c' showing force-displacement curves, according to the embodiments disclosed in FIGS. 1 to 19. FIGS. 21a-21d show a cartridge needle insertion process with the cartridge needle axis 53 oblique to the insertion axis 52 with the cartridge needle insertion mechanism and corresponding schematic diagrams 21a'-21c' showing force-displacement curves according to the embodiments disclosed in FIGS. 1 to 19.

FIGS. 22a-22d show a cartridge needle insertion process with the cartridge needle axis 53 oblique to the insertion axis 52 with a cartridge needle insertion mechanism having a compliant coupling between a cartridge needle holder and a cartridge needle slider and corresponding schematic diagrams 22a'-22c' showing force-displacement curves according to the embodiments that will be presented in FIGS. 23 to 29 and according to implementations of the present disclosure. The force-displacement curves for the forces along (N), and forces perpendicular (Q) to the insertion axis 52 are presented in the schematic diagrams 20a'-20c', 21a'-21c', 22a'-22c' next to each of FIGS. 20a-20c, 21a-21c, and 22a-22c.

Figures 20A, 20B, 20C, 20D:
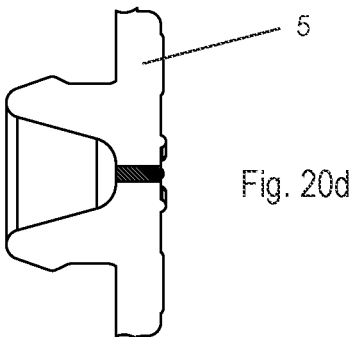
FIGS. 20a, 20b, and 20c illustrate a cartridge needle insertion process, with a cartridge needle axis parallel to the insertion axis and the forces in the insertion direction (N) and perpendicular to the insertion direction (Q), where the needle tip penetrates a top surface of the septum (FIG. 20a); the needle tip penetrates through the septum (FIG. 20b); and the needle fully penetrates through the septum (FIG. 20c)
FIG. 20d illustrates a cross-section of the septum when the cartridge needle has been inserted with the cartridge needle axis parallel to the insertion axis.

When the needle 70 or cartridge needle is inserted with its needle axis 53 being equal to the insertion axis 52, then there are no perpendicular forces Q acting on the needle 70, as reflected in the schematic diagrams of FIGS. 20a-20c, and the penetration hole in the septum approximately equals the cross-section of the cartridge needle, see FIG. 20d. The forces N acting along the insertion axis initially rise (FIG. 20a) as the tip of the needle penetrates the surface of the septum 5, and the force N reaches a maximum value once the tip fully penetrates through the septum (FIG. 20b). The frictional forces between the outside surface of the needle 70 and the inside surface of the elastically deformed penetration hole ensures that a constant normal force N needs to be supplied by the insertion mechanism (FIG. 20c).

When a needle 70 is inserted with its needle axis 53 being at an angle to the insertion axis 52, then perpendicular forces Q will act on the needle 70, FIGS. 21a-21c, and the penetration hole in the septum is larger compared to the ideal situation described previously where the needle axis is perpendicular to the septum (compare FIGS. 20d and 21d). The cross-sectional area of the passage in the septum 5 is enlarged as the angulated (and sharp) needle tip cuts through the septum (FIG. 21d). The force profile for the penetration forces N along the insertion axis is more or less equal to the profile for a parallel insertion, e.g., compare the force profiles N in FIGS. 20c and 21c. For the off-axis insertion, needle penetration forces perpendicular the insertion axis will occur and those are schematically represented by a non-linear curve rising to a maximum value once the needle has fully penetrated through the septum (FIG. 21c).

In the situation where the needle penetration forces Q oriented perpendicular to the insertion axis are compensated for, then the off-axis penetration forces are reduced (FIG. 22c). The needle penetration forces Q are reduced but not completely eliminated as the off-axis insertion angle is not eliminated since the insertion mechanism is not an alignment mechanism. The flexibility in the insertion mechanism including the compliant coupling may ensure that cartridge needle tip is not pushed through the septum (thereby cutting a larger hole as in FIG. 21d), but, nicely cuts through the septum as the center of the cartridge needle holder is moved with respect to the cartridge needle slider thereby minimizing the hole in the septum and thereby minimizing the leakage risk.

Figure 23:
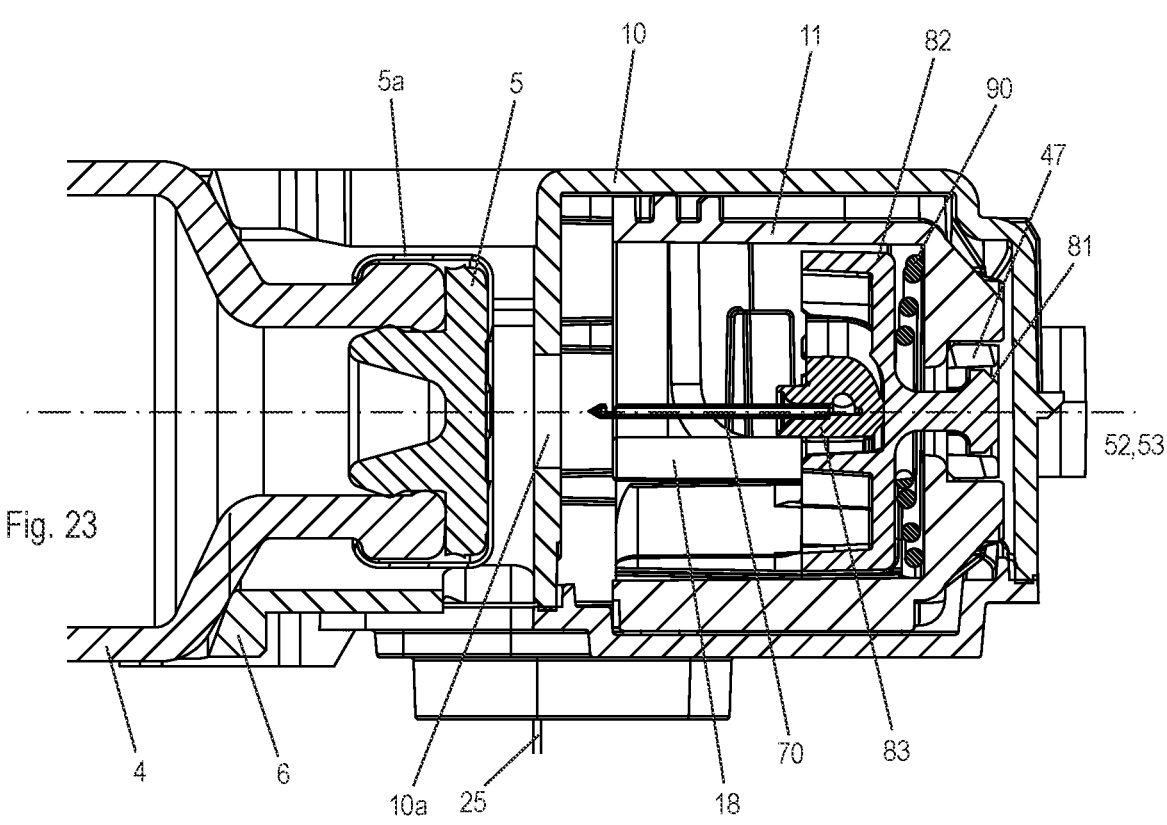
FIG. 23 illustrates a cross-section of the cartridge needle insertion mechanism with a complaint coupling mechanism when the cartridge needle holder is in the retracted (first) position.
Figure 24:
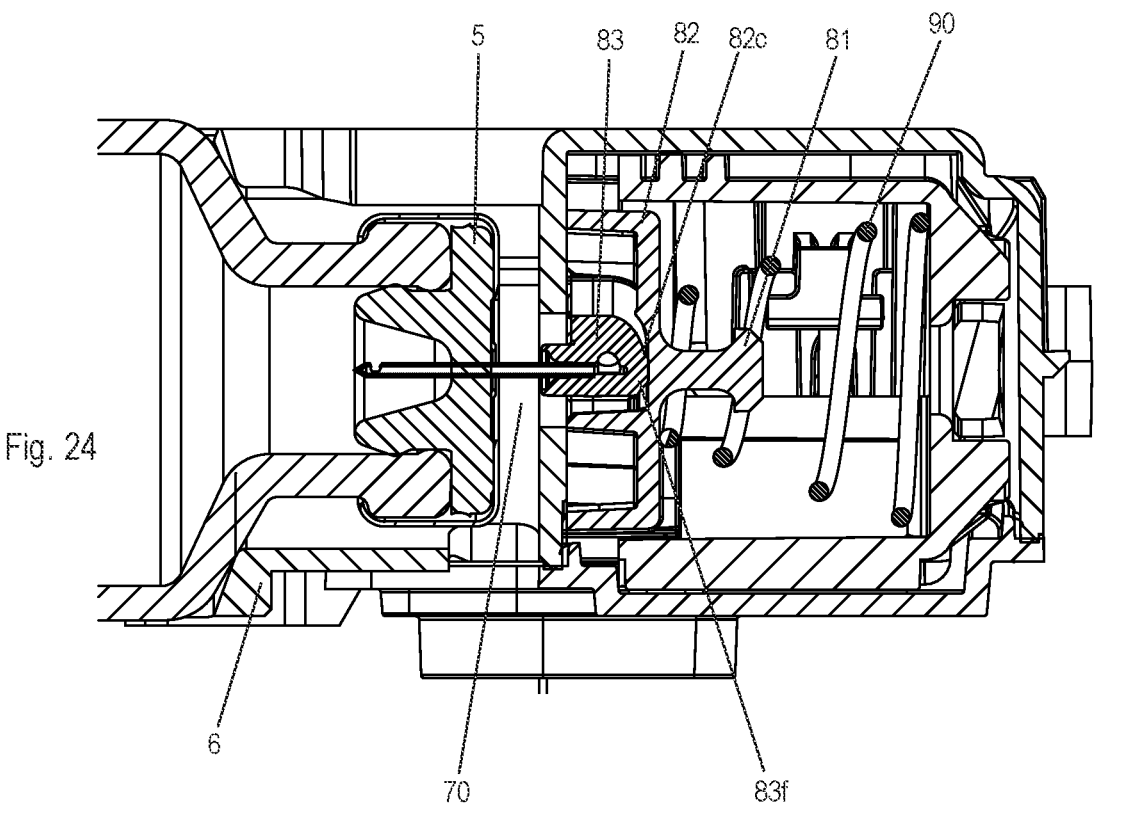
FIG. 24 illustrates a cross-section of the cartridge needle insertion mechanism with a complaint coupling mechanism when the cartridge needle holder is in the inserted (second) position, where the needle axis coincides with the insertion axis.
Figure 25:
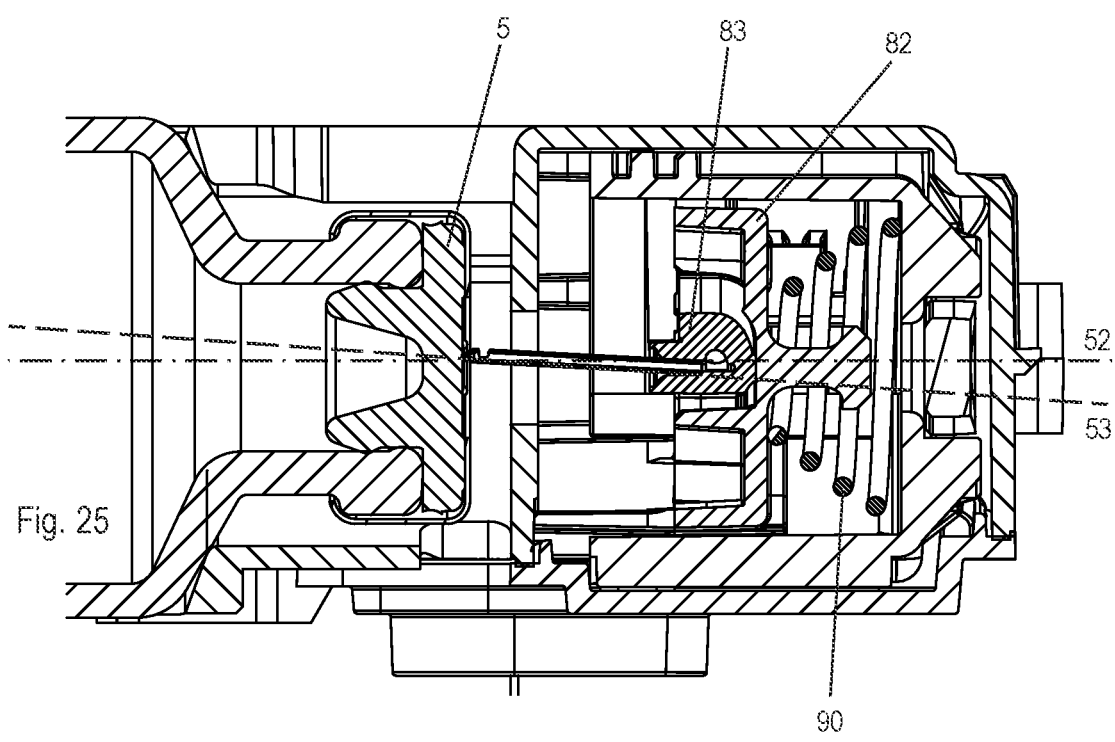
FIG. 25 illustrates a cross-section of the cartridge needle insertion mechanism with a complaint coupling mechanism when the cartridge needle holder has left the retracted (first) position, where the needle axis is oblique to the insertion axis.
Figure 26:
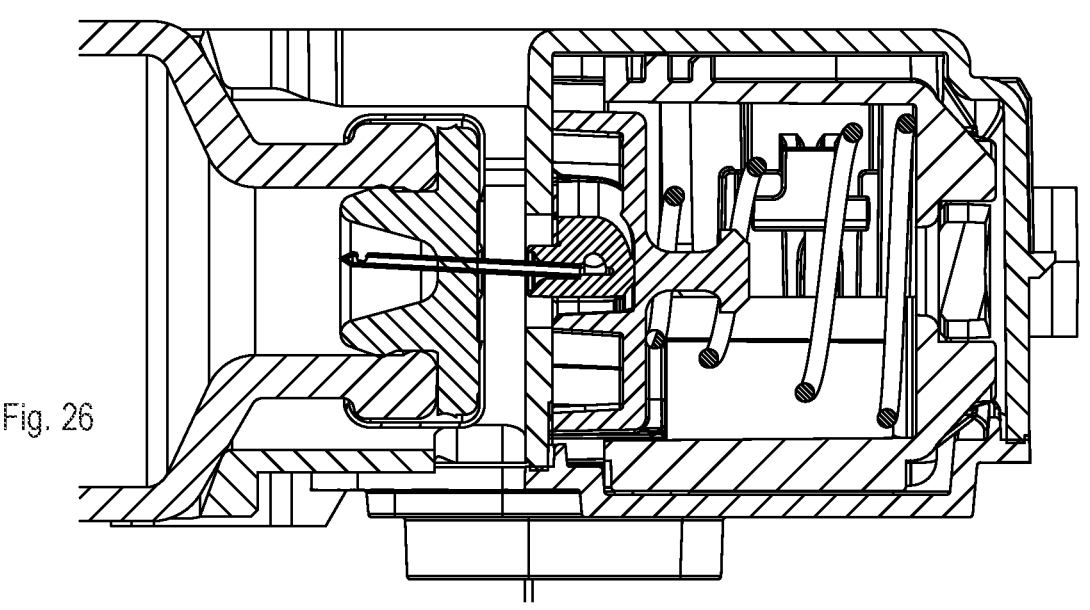
FIG. 26 illustrates a cross-section of the cartridge needle insertion mechanism with a complaint coupling mechanism when the cartridge needle holder is in the inserted (second) position, where the needle axis is oblique to the insertion axis.
Figure 27:
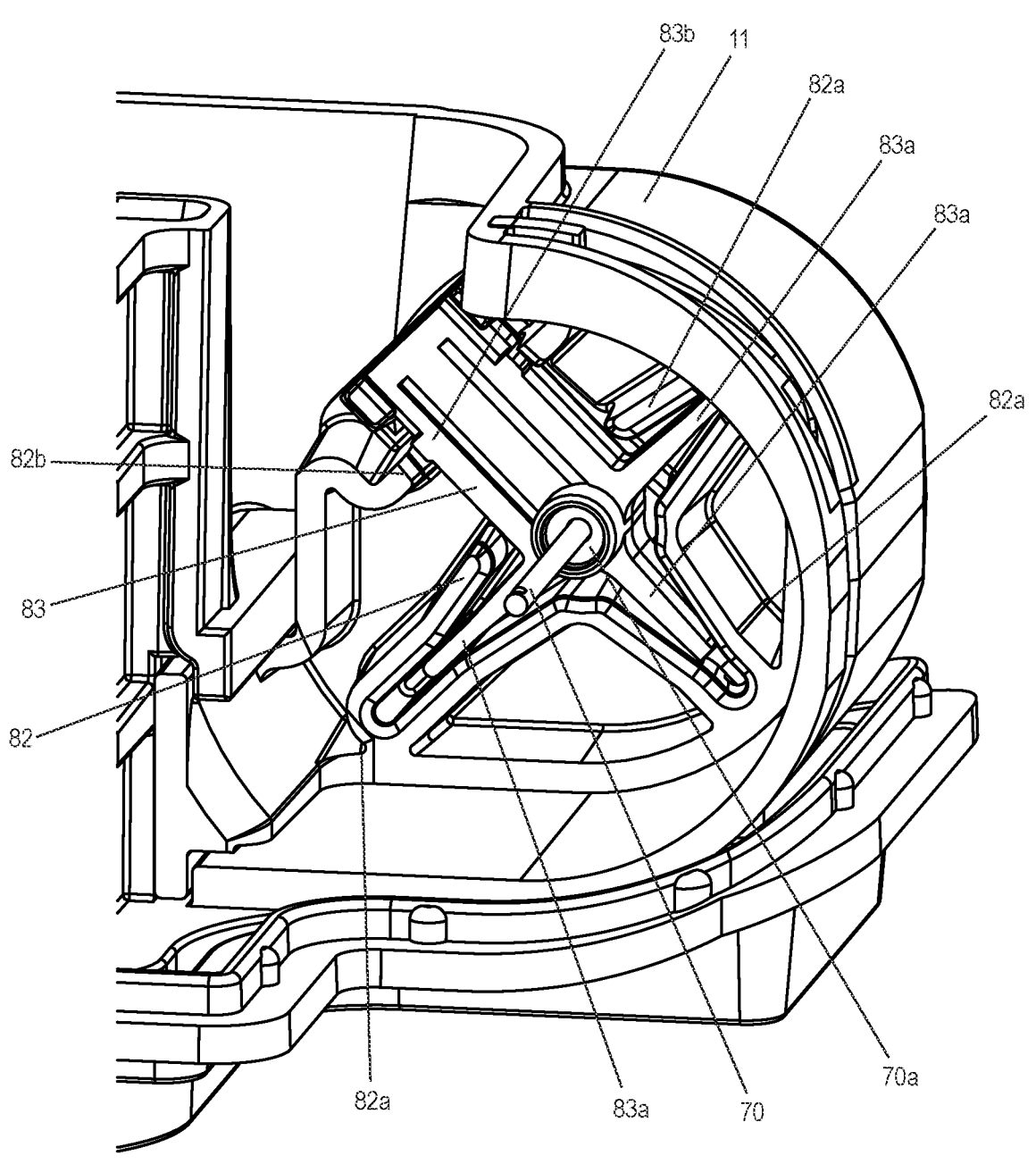
FIG. 27 illustrates a three-dimensional view of the compliant coupling mechanism.
Figure 28:
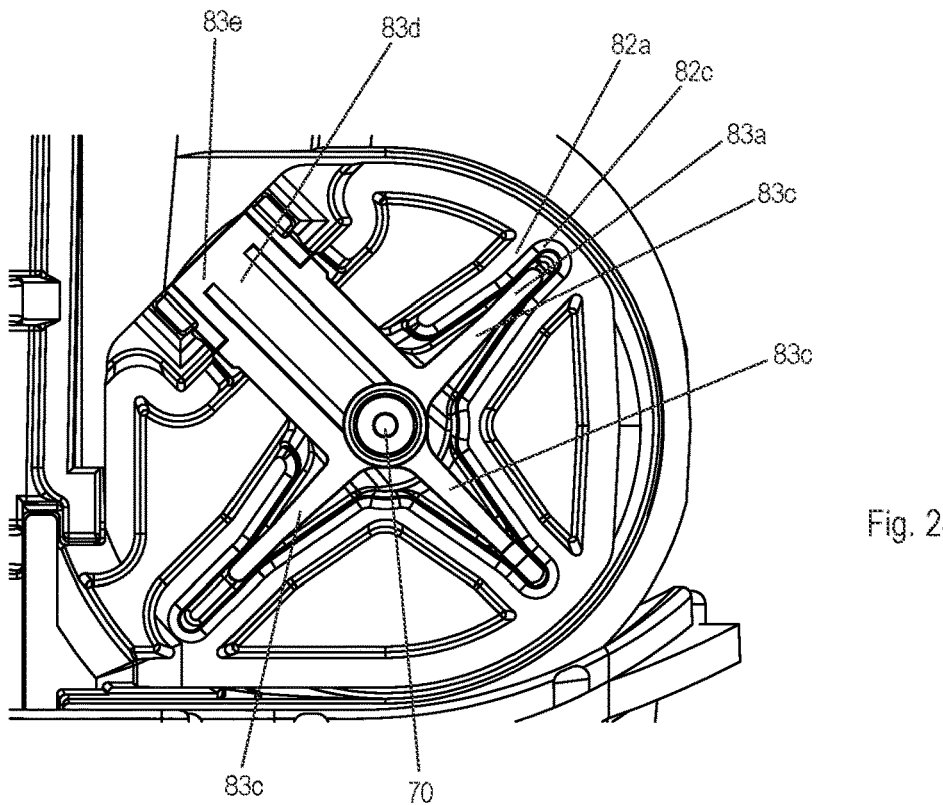
FIG. 28 illustrates a compliant coupling mechanism in a non-deformed state.
Figure 29:
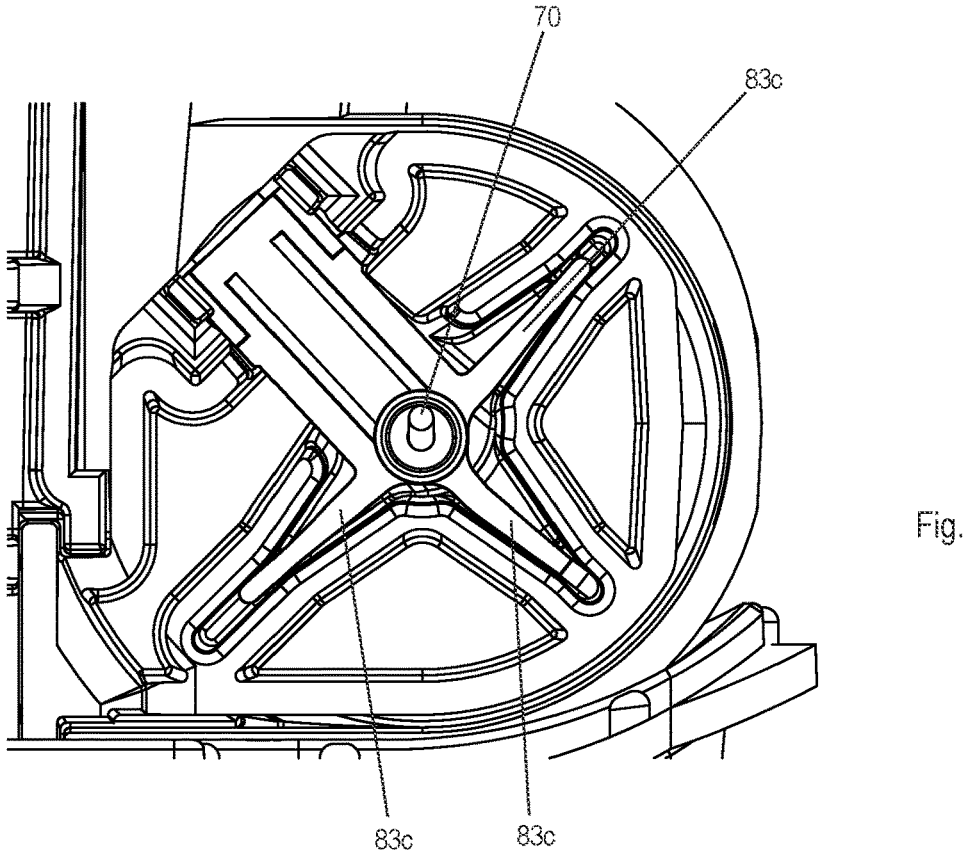
FIG. 29 illustrates a compliant coupling mechanism in a deformed state.

An embodiment for a needle insertion mechanism with a compliant coupling will be presented in the following FIGS. 23 to FIG. 29. The cartridge needle carrier 80 in the previous embodiment (FIG. 10) has been split into two separate parts, a cartridge needle holder 83 and a cartridge needle slider 82. The cartridge needle holder 83 may hold the proximal section of the needle 70 opposite from the needle or spike tip. The cartridge needle slider 82 may be engaged with the housing 10, 11 using a linear guide. The linear guide may be oriented parallel to the insertion axis 52, such as parallel to the longitudinal axis of the cartridge. The housing may include a linear guide or groove 18 engaging a linear protrusion on the cartridge needle slider 82. The groove-protrusion combination may be reversed as well, and there may be a plurality of linear guides for guiding the cartridge needle slider 82 along the insertion axis 52. The cartridge needle holder 83 may include a bore for receiving the proximal section of the needle and the needle may be fixed inside the bore using a press-fit connection, adhesive, barbed hooks extending from the needle or the plastic material for the cartridge needle holder maybe be injection molded around the cartridge needle 70. In case an adhesive is used this may be a flexible adhesive (after curing) which may provide an extra dampening effect during insertion through the septum 5 into the cartridge 4. The bore in the cartridge needle holder 83 may be directly or indirectly connected to the flexible tube 85 of the fluid conduit. The section of the cartridge needle holder 83 that is opposite to the bore may be closed and may include a stop surface 83f abutting a counter stop surface 82c on the cartridge needle slider 82. The spring 90 may be compressed between the housing 11 and the cartridge needle slider 82 as the counter surface 81 of the cartridge needle slider 82 engages the retaining surface 47 of the slider 40 to keep the cartridge needle 70 in the retracted position (FIG. 23). When the slider 40 is moved by rotation of the cam shaft 15 activating the rack-and-pinion of the gear wheel 16 and gear rack 41 (FIGS. 16 and 17), then the engagement of the retaining surface 47 and counter surface 81 between the slider 40 and the cartridge needle slider 83 may be released and spring 90 decompressed. The spring 90 may push on the cartridge needle slider 83 and due to the abutment 82c, 83f, the cartridge needle holder 83 may be forced to be moved together with the cartridge needle slider 82 towards the cartridge 4 or cartridge holder 6 while the cartridge needle slider 82 may be guided by the linear guide 18. The abutment 82c, 83f ensures that needle penetration forces N, along the insertion axis are absorbed as the needle penetrates the septum. The tip of the cartridge needle 70 may pass through a passage 10a of the housing 10 and penetrate through the septum 5 that is held onto the cartridge 4 by a crimp 5a. In FIGS. 23 and 24, the axis for the needle 53 is parallel to the insertion axis 52 whereas an off-axis insertion is shown in FIGS. 25 and 26 where the needle axis 53 has an inclined angle with respect to the insertion axis 52. Details for the compliant coupling between the cartridge needle slider 82 and the cartridge needle holder 83 are shown in FIGS. 27 to 29.

The cartridge needle holder 83 may include a plurality of, e.g., four, first coupling members (coupling parts, couplers) 83a, 83b shaped as protrusions that radially extend outwards from the cartridge needle axis. A portion of the, e.g., three, first coupling members 83a may include a flexible arm 83c, whereas one of the other, e.g. the fourth, first coupling members 83b may be a rigid arm 83d and may include a passage 83e for connection to the tubing 85 of the fluid path. The passage 83e may connect the proximal end of the cartridge needle 70 to the tubing 85. Each of the plurality of, e.g. all four, of the first coupling members 83a, 83b of the cartridge needle holder 83 may engage one of a plurality of, e.g. one of four, second coupling members (coupling parts, couplers) 82a, 82b on the cartridge needle slider 82. Where four first coupling members are provided by the cartridge needle holder 83, three of the four second coupling members 82a of the cartridge needle slider 82 may be configured to receive the first coupling members 83a including the flexible arm 83c of the cartridge needle holder 83, whereas one of the four second coupling members 82b of the cartridge needle slider 82 may engage the rigid first coupling member 83b including the passage 83e of the cartridge needle holder 83. The three second coupling members 82a of the cartridge needle slider 82 may be shaped as a longitudinal recess or pocket. All four second coupling members of the cartridge needle slider 82 may be configured to be rigid or semi-rigid when engaging the four first coupling members of the cartridge needle holder 83. The engagement between the first coupling members 83a including the flexible arm 83c and the rigid walls in the recess or pocket of the second coupling members 82a may be such that there may be a frictional engagement when the coupling members move or slide with respect to each other. Optionally, the flexible arms 83c may bend when engaging the second coupling members 82a. The frictional and/or elastic forces required may be used to compensate for needle penetration forces as the cartridge needle slider 82 moves from the first (not inserted) to the second (inserted) position. The rigid first coupling member 83b including the passage 83e may be configured such that there may be relative rotation or tilting with respect to the rigid second coupling member 82b without any elastic deformation. The rigid second coupling member 82b may be shaped as a cutout in the cartridge needle slider 82. The first coupling members 83a of the cartridge needle holder 83 may be shaped as wings or blades that radially extend outwards and may engage complementary pockets of the second coupling members 82a of the cartridge needle slider 82. The wings or blades of the first coupling members 83a may be oriented parallel to the insertion axis, optionally, one or all of the three first coupling members 83a may be tilted with respect to the insertion axis. The surfaces of the first and second coupling surfaces 83a, 82a may be textured, roughened or sand blasted to fine-tune the frictional engagement. Alternatively, a lubricant, for example a silicone oil, may be used to reduce friction. The first and second coupling members 83a, 82a may be made from a polymeric material that may be friction optimized by adding a friction agent such as silicone oil, Teflon, fluoro(co)polymers or an olefinic wax. The cartridge needle holder 83 may be snap-fitted into the cartridge needle slider 82 using hooks, catches or flexible arms on the cartridge needle slider and/or the cartridge needle holder. The snap-fit connection may improve handling during assembly and may reduce the play between the stop surface 83*f* and the counter stop surface 82*c*. Optionally, the cartridge needle 70 may be adhesively and/or flexibly connected to the cartridge needle holder 83 using a flexible connector 70*a* such as a flexible adhesive or other flexible bonding material. FIG. 28 illustrates the compliant coupling arrangement between the cartridge needle holder 83 and the cartridge needle slider 82 in the non-deformed state, where the cartridge needle 70 inserts parallel to the insertion axis. For an off-axis insertion, the compliant coupling is shown in the deformed state in FIG. 29.

Variations of the embodiments presented in FIGS. 23 to 29 can be envisioned without deviating from the present disclosure. For example, the number of first and second coupling members forming pairs of coupling members may be provided, for example two, three or five pairs can be envisioned. Also the number of rigid and flexible coupling members may be varied. It may be that the cartridge needle slider includes two separate cartridge needles and the cartridge needle may be a pencil tip needle.

While the implementations of the present disclosure have been described in detail in the drawings and foregoing description, such description is to be considered illustrative or exemplary and not restrictive. Variations to the disclosed embodiments can be understood and effected by those skilled in the art and practicing the claimed invention, from a study of the drawings, the disclosure, and the appended claims.

LIST OF REFERENCE SIGNS

| 2 | insertion and retraction module |
|---|---|
| 3 | insertion and retraction mechanism |
| 4 | product container, cartridge |
| 5 | septum (pierceable wall) |
| 5a | crimp |
| 6 | cartridge holder |
| 10 | housing |
| 10a | passage |
| 11 | first housing |
| 11a | axial stop |
| 11b | stop surface |
| 12 | second housing |
| 14 | linear guide |
| 15 | drive shaft, cam-shaft |
| 16 | gear wheel/pinion |
| 17 | coupling member |
| 18 | linear guide/groove |
| 20 | needle carrier, needle holder |
| 21 | counter stop surface |
| 22 | stop surface |
| 23 | stop surface |
| 25 | needle, skin insertion needle |
| 30 | spring/lever spring |
| 31 | first spring member |
| 31a | first spring arm |
| 31b | first helical spring section |
| 32 | second spring member |
| 32a | second spring arm |
| 32b | second helical spring section |
| 33 | interconnecting section |
| 40 | control element/slider |
| 41 | gear rack/rack |
| 42 | cap |
| 43 | main body |
| 44 | (first) stop surface |

-continued

LIST OF REFERENCE SIGNS

| 45 | linear guide |
|---|---|
| 46 | linear guide |
| 47 | retaining surface |
| 50 | first intermediate member |
| 51 | counter stop surface |
| 52 | Insertion axis |
| 53 | Cartridge needle axis |
| 60 | second intermediate member |
| 61 | counter stop surface |
| 70 | hollow needle, cartridge needle |
| 70a | flexible connector |
| 80 | needle carrier, cartridge needle carrier |
| 81 | counter surface |
| 82 | cartridge needle slider |
| 82a | second coupling member, coupling part or coupler |
| 82b | second coupling member, coupling part or coupler |
| 82c | counter stop surface |
| 83 | cartridge needle holder |
| 83a | first coupling member, coupling part or coupler |
| 83b | first coupling member, coupling part or coupler |
| 83c | flexible arm |
| 83d | rigid arm |
| 83e | passage |
| 83f | stop surface |
| 85 | flexible tube |
| 90 | spring |

What is claimed is:

1. An assembly for a cartridge needle insertion mechanism comprising:

a housing;

a cartridge needle defining a cartridge needle axis;

a cartridge closed by a septum;

a cartridge needle slider linearly guidable by the housing along an insertion axis and movable by a driver from a first position in which the cartridge needle does not penetrate the septum to a second position in which the cartridge needle penetrates the septum;

a cartridge needle holder holding the cartridge needle and operatively coupled with the cartridge needle slider, the cartridge needle holder and the cartridge needle movable together with the cartridge needle slider along the insertion axis from the first position to the second position; and a compliant coupling comprising a first coupling member on the cartridge needle holder and a second coupling member on the cartridge needle slider, the first coupling member and the second coupling member configured to elastically engage and/or configured to engage in a linear or rotational friction fit engagement in a plane parallel to the insertion axis, wherein the compliant coupling is configured to facilitate a movement of the cartridge needle holder with respect to the cartridge needle slider when moved into the second position, thereby compensating for needle penetration forces oriented perpendicular to the insertion axis.

2. The assembly according to claim 1, wherein the movement of the cartridge needle holder with respect to the cartridge needle slider is perpendicular to the insertion axis, or the movement is a pivoting movement of the cartridge needle holder around the insertion axis, or the cartridge needle holder rotates around the insertion axis.

3. The assembly according to claim 1, wherein the first coupling member comprises an at least partially elastically and/or plastically deformable protrusion radially extending from the cartridge needle holder and engages the second coupling member shaped as a rigid surface on the cartridge needle slider being oriented parallel to the insertion axis.

4. The assembly according to claim 1, wherein the cartridge comprises a barrel defining a cartridge axis and the cartridge is in a fixed position with respect to the housing, and wherein the cartridge axis is aligned with the insertion axis when the cartridge needle slider is in the first position.

5. The assembly according to claim 1, wherein the cartridge needle slider and the cartridge needle holder are coaxially arranged around the insertion axis when the cartridge needle slider is in the first position.

6. The assembly according to claim 5, wherein the cartridge needle holder is moved out of the coaxial arrangement with respect to the cartridge needle slider when the needle axis is not parallel to the insertion axis when the cartridge needle slider is moved into the second position thereby generating needle penetration forces perpendicular to the insertion axis and deforming the compliant coupling.

7. The assembly according to claim 1, wherein the cartridge needle holder is axially fixed to the cartridge needle slider while allowing movement with respect to the cartridge needle holder perpendicular to the insertion axis, or a pivoting or a rotational movement around the insertion axis against a bias or resistance of the compliant coupling, and wherein the cartridge needle slider is linearly guided by the housing by a splined engagement.

8. The assembly according to claim 1, wherein the cartridge needle is connected to the cartridge needle holder by an elastic member.

9. The assembly according to claim 8, wherein the elastic member comprises an elastic adhesive.

10. The assembly according to claim 1, wherein the driver is a spring located between the housing and the cartridge needle slider and acting on the housing and the cartridge needle slider, the spring being retained in a compressed state to provide a biasing force on the housing and the cartridge needle slider when the cartridge needle slider is held in the first position with respect to the housing by a releasable locking feature.

11. The assembly according to claim 1, wherein the first coupling member of the compliant coupling is hollow and fluidly couples the cartridge with the cartridge needle.

12. The assembly according to claim 1, wherein the cartridge needle is a hollow needle with a sharpened tip, wherein the sharpened tip has a closed end or an open end.

13. The assembly according to claim 1, wherein the assembly forms a portion of an injection device, wherein the injection device is a prefilled patch injection device comprising a skin adhesive surface and a skin needle configured to move from a needle retracted position in the housing to a needle inserted position at least partially outside of the housing after the cartridge needle slider has moved from the first position to the second position.

14. The assembly according to claim 1, wherein the first coupling member comprises a rigid protrusion radially extending from the cartridge needle holder engaging the second coupling member shaped as an at least partially elastically and/or plastically deformable surface on the cartridge needle slider being oriented parallel to the insertion axis.

15. An assembly for a cartridge needle insertion mechanism, comprising:

a housing;

a cartridge needle defining a cartridge needle axis;

a cartridge closed by a septum;

a cartridge needle slider linearly guidable by the housing along an insertion axis and movable by a driver from a first position in which the cartridge needle is not penetrating the septum to a second position in which the cartridge needle penetrates the septum;

a cartridge needle holder holding the cartridge needle, the cartridge needle holder operatively coupled with the cartridge needle slider such that movement of the cartridge needle slider carries the cartridge needle holder along the insertion axis from the first position to the second position to thereby cause the cartridge needle to penetrate the septum; and a compliant coupling comprising a first coupling member on the cartridge needle holder and a second coupling member on the cartridge needle slider, wherein the first coupling member comprises a protrusion radially extending from the cartridge needle holder, whereby the protrusion is at least partially elastically and/or plastically deformable and engages the second coupling member shaped as a rigid surface on the cartridge needle slider being oriented parallel to the insertion axis, or wherein the first coupling member comprises a rigid protrusion radially extending from the cartridge needle holder engaging the second coupling member shaped as an at least partially elastically and/or plastically deformable surface on the cartridge needle slider being oriented parallel to the insertion axis, wherein the first coupling member and the second coupling member are configured to elastically engage and/or configured to engage in a linear or rotational friction fit engagement in a plane parallel to the insertion axis, and wherein the compliant coupling is configured to facilitate a movement of the cartridge needle holder with respect to the cartridge needle slider when moved into the second position, thereby compensating for needle penetration forces that are oriented perpendicular to the insertion axis.

\* \* \* \* \*